US 6,475,215 B1
Nov. 5, 2002

(12) United States Patent
Tanrisever

(54) QUANTUM ENERGY SURGICAL DEVICE AND METHOD

(76) Inventor: Naim Erturk Tanrisever, Bostan Tuccari Sokak 7/22, 81110 Bostanci, Istanbul (TR)

(*) Notice: Subject to any disclaimer, the term of this patent is extended or adjusted under 35 U.S.C. 154(b) by 114 days.

(21) Appl. No.: 09/689,216

(22) Filed: Oct. 12, 2000

(51) Int. Cl.[7] ............................................. A61B 18/12
(52) U.S. Cl. .......................... 606/45; 606/49; 606/32; 606/39; 606/40
(58) Field of Search ................. 606/27, 45, 32, 606/39, 40

(56) References Cited

U.S. PATENT DOCUMENTS

| | | | |
|---|---|---|---|
| 3,434,476 A | * 3/1969 | Shaw et al. | 606/22 |
| 3,838,242 A | 9/1974 | Goucher | 219/121 P |
| 3,903,891 A | * 9/1975 | Brayshaw | 606/27 |
| 3,938,525 A | 2/1976 | Coucher | 128/303.1 |
| 3,991,764 A | 11/1976 | Incropera et al. | 128/303.1 |
| 4,225,769 A | * 9/1980 | Wilkins | 219/121.36 |
| 4,781,175 A | * 11/1988 | McGreevy et al. | 606/40 |
| 4,855,563 A | 8/1989 | Beresnev et al. | 219/121.39 |
| 5,587,093 A | * 12/1996 | Aston | 219/121.36 |
| 5,680,014 A | * 10/1997 | Miyamoto et al. | 219/121.11 |
| 5,720,745 A | * 2/1998 | Farin et al. | 606/41 |
| 5,843,079 A | 12/1998 | Suslov | 606/43 |
| 5,888,198 A | 3/1999 | Eggers et al. | 604/114 |

FOREIGN PATENT DOCUMENTS

WO    WO 99/12692    3/1999

OTHER PUBLICATIONS

Link WJ, Zook EG, Glover JL, "Plastic Scapel Excision of Burns, An Experimental Study" (Abstract), *Plast Surg*, 1975 Jun.; 55(6):647–63.

Link WJ, Incorpera FP, Glover JL, "The Plastic Scalpel" (Abstract), *Med Prog Technol* 1976;4(3):123–31.

Link WJ, Incropera FP, Glover JL, "A Plasma Scalpel: Comparison of Tissue Damage and Wound Healing With Electrosurgical and Steel Scalpels" (Abstract), *Arch Surg*, 1976 Apr.;111(4):392–7.

Payne NS, Tindall GT, Fleischer AS, Mirra SS, "Evaluation of the Plasma Scalpel for Intracranial Surgery: A Pilot Study" (Abstract), *Surg Neurol* 1979 Sep.;12(3):247–50.

"The Plasma Scalpel: A New Thermal Knife" (Abstract), *Lasers Surg Med* 1982;2(1):101–6.

* cited by examiner

*Primary Examiner*—Lee Cohen
*Assistant Examiner*—Henry M. Johnson, III
(74) *Attorney, Agent, or Firm*—RatnerPrestia

(57) ABSTRACT

A surgical apparatus adapted to emit a plurality of high-energy inert gas atoms, such as argon, in a stream for cutting, cauterizing, or evaporating tissue. The apparatus comprises an inert gas supply, a plasma cell in communication with the inert gas source for imparting energy to the inert gas atoms and defined in part by a positive electrode and a negative electrode, at least one power supply electrically connected between the positive and negative electrodes, and means for directing the energized inert gas atoms at a target. The power supply provides initially an ionization voltage between the negative and positive electrodes to initiate a plasma from the inert gas in the plasma cell, and subsequently a pulsed voltage curve that sustains the plasma at a predetermined energy level. Methods for performing surgical procedures using the surgical apparatus for cutting, cauterizing, and/or evaporating portions of body tissue are also described.

57 Claims, 19 Drawing Sheets

QUANTUM ENERGY SURGICAL DEVICE AND METHOD

TECHNICAL FIELD

This invention relates generally to surgical equipment, and more particularly to a surgical device used for cutting, coagulating and evaporating tissues.

BACKGROUND OF THE INVENTION

Traditional methods of surgery have long included cutting tissue with mechanical knives. One of the fundamental problems with mechanical knives, however, is that they create bleeding while cutting the tissue. In addition to the unavoidable and undesirable loss of blood, there is an additional risk of not being able to stop bleeding in certain tissues such as the brain, and in certain organs such as the liver, spleen, and pancreas. Furthermore, where the object of the surgery is to remove cancerous growths, there is a risk of transferring cancer cells through the open channels, such as veins, arteries, bile ducts, or lymphatic channels, created by the mechanically cut tissue.

In general, cutting tissue with a knife can be described as applying energy with mechanical force in the form of the hard, sharp edge of the metal knife applying mechanical pressure against a thin line of a softer tissue to break the tissue locally. Energies and mechanisms in addition or instead of mechanical energy and mechanical pressure may be used in surgery, however, such as but not limited to, mechanical impact, or thermal energy mechanisms such as low-temperature freezing or high-temperature burning.

For example, for hard tissue such as bone, a saw may be used to break the bone using the mechanical impact and momentum of the hard, metal sawteeth, also creating thermal energy. Ultrasonic vibration tools also apply mechanical impact to destroy tissues that are relatively softer than the mechanical tool. Cryogenic equipment cools tissue to a freezing temperature to destroy it. Thermal energy transferred from a metal mass may be used to destroy unwanted tissues and simultaneously stop bleeding of using a burning mechanism. When the metal mass is heated with electrical energy, it is referred to as bipolar cauterizing equipment. Thermal energy can also be transferred to the tissue by electrical discharge.

Some high-temperature, thermal energy technologies include the use of electrons, ions, atoms or photons to apply the thermal energy. Monopolar cauterizing equipment transfers energy to the tissue using single electrons and ions of gas atoms. Lasers use the conversion of single photon energy in packed photons to thermal energy to hit the tissues to destroy them or to stop their bleeding.

The above energies and mechanisms may be combined, such as, for example, as is demonstrated by cryogenic or ultrasonic knives. For all of the above technologies in which a mass of matter such as a metal or plastic is used to transfer thermal energy to or from the tissues, however, a relatively large amount of energy is transferred. Technologies that use particles like electrons, ions, atoms or photons for energy transfer, on the other hand, transfer a relatively small amount of energy. For illustrative purposes, the amount of total thermal energy transferred to a tissue can be calculated as the number of atoms applied times the energy per atom, assuming that at the moment the metal or mass of matter touches the tissue, its total energy will be transferred to the tissue. Thus, the use of a cubic millimeter of titanium for heat transfer can be compared with use of the cubic millimeter of an inert gas, such as in a plasma device. One mole of argon gas weighs about 40 grams, and its volume is 22.4 litres (22,400,000 cubic millimeters), but one mole of titanium weighs about 48 grams and its volume is 10.55 cubic centimeters (10,550 cubic millimeters). Given that one mole of metal has $6.022 \times 10^{23}$ atoms, the thermal energy transferred at the moment of contact with the cubic millimeter of titanium is the thermal energy of approximately $5.7 \times 10^{19}$ atoms. A cubic millimeter of any inert gas has only $2.7 \times 10^{16}$ atoms, which is more than two thousand times less than the number of atoms in a cubic millimeter of a relatively light metal. It is typically not practically possible to apply a titanium piece to the tissue smaller than a cubic millimeter, but it is possible to make a momentary application of an inert gas to an area of tissue less than a cubic millimeter. Thus, even if the temperature of the titanium is 1000° C. and the temperature of an inert gas is 10,000° C., it is possible to focus the total energy applied by the gas to a thousand times less than the amount of energy applied by the metal. In any event, one can not transfer such a high per-atom or "quantum" energy with a metal because the metal melts once it reaches its melting temperature.

Knives, saws, bipolar surgical equipment, and ultrasonic equipment transfer thermal energy using masses of matter. The transfer of thermal energy using monopolar surgical equipment comprises the transfer of thermal energy from electrons, ions, and some of the atoms of the tissue in the treated area. This means that the total energy transferred can be controlled quite well. One of the disadvantages of monopolar equipment, however, is the technical necessity that a second pole must be connected to the body of the patient. This connection can be far away from the tissue operated, or close to it. In both cases, other tissues may be negatively affected by the electrical currents passing through those tissues. Where the second pole connection is far away from the tissue on which the operation is performed, the currents may affect a large amount of other tissues. Where the second pole connection is close, tissue closer to the operation point is affected. This makes application of monopolar technology to sensitive tissues like brain tissues essentially impossible. Additionally, particle energies transferred by electrons and ions can be quite high, on the order of 10–20 electron volts.

Using photons for energy transfer, such as with lasers, solves both the total energy control problem and per-particle energy control problem. But when the laser beam hits the tissue, individual photons are obtained and the penetration of the photons through the tissue molecules generally cannot be controlled enough to assure that there is no molecular harm to tissues far behind the application area.

In general, the application of thermal energy destroys tissues, dehydrating them by vaporizing water molecules, and destroying the bio-molecules, breaking them into smaller molecules and vaporizing a small part of them.

Plasma technology has previously been proposed for use in surgical equipment, as detailed, for example, in U.S. Pat. Nos. 3,434,476, 3,838,242; 3,938,525; and 3,991,764. A "plasma" is defined as essentially "a high-temperature, ionized gas composed of electrons and positive ions in such relative numbers that the gaseous medium is essentially electrically neutral." Webster's New World College Dictionary, 3d Edition, 1997. Plasma surgical equipment, also referred to as "plasma scalpels," essentially generate a small, hot gas jet that can simultaneously cut tissue and cauterize blood vessels. Such plasma devices typically use direct current (D.C.) constant voltage sources or radio frequency (rf) sources to provide the energy to the plasma.

Despite early experimentation on animals, it is believed that plasma surgical equipment has not become commercially available for use on humans possibly because of technical issues relating to the relatively large size of the hand-pieces used to direct the plasma beam at the treatment area, the relatively uncontrolled high total energy, relatively uncontrolled quantum energy, and relatively uncontrolled "blast effect" of the plasma beam causing undesirable destruction of surrounding tissue.

Thus, there is still a need in the art to provide improved surgical cutting technology, and particularly improved plasma cutting technology and tissue evaporation (sputtering) technology for surgical applications.

SUMMARY OF THE INVENTION

One aspect of the invention comprises a surgical apparatus adapted to emit a plurality of high-energy inert gas atoms in a stream, the apparatus comprising an inert gas source and a plasma cell in communication with the inert gas source for imparting energy to the inert gas atoms. The plasma cell is defined in part by a positive electrode and a negative electrode. At least one power supply is electrically connected to the between the positive and negative electrodes. The power supply is adapted to provide (a) initially an ionization voltage between the negative and positive electrodes to initiate a plasma from the inert gas in the plasma cell, and (b) subsequently a pulsed voltage curve that limits the plasma to a predetermined energy level. The pulsed voltage curve applied on the plasma cell through an inductance coil creates a current curve and a voltage curve that are both sharkfin-shaped. The difference in voltage between the pulsed voltage curve input to the inductance coil and the sharkfin-shaped output from the coil arises from the dampening effect of the coil.

The apparatus may further comprise a hand-piece having a tubular body comprising therein the plasma cell, and a tip comprising a channel in communication with the plasma cell for emission of the inert gas atoms from the tip. A portion of the tip disposed inside the hand-piece body may comprise the positive electrode. A control system may be connected to the gas supply and to the power supply. The control system has at least one user interface and a plurality of energy settings. The control system is adapted to vary the voltage curve and the inert gas flow to provide a user-selected energy level in said plasma. The control system may comprise a programmable controller, a quantum energy control user interface connected to the programmable controller, and a total energy control user interface connected to the programmable controller.

The quantum energy control user interface may comprise a control panel with a plurality of switches, each switch corresponding to a desired quantum energy level and the total energy control user interface may comprise a start switch, a first switch for increasing power, a second switch for decreasing power, and a stop switch.

The hand-piece may have a cooling system comprising a water circulation system within the hand-piece. The hand-piece may be detachable and may comprise materials of construction adapted to be chemically or thermally sterilized. The tip may comprise an elongated, curved extension.

Another aspect of the invention comprises a method for performing a surgical procedure of cutting, cauterizing, or evaporating a portion of a body tissue, or a combination thereof, using the surgical apparatus of this invention. The method comprises providing inert gas flow into the plasma cell, initially applying from the power supply an ionization voltage between the negative and positive electrodes which initiates a plasma from the inert gas in the plasma cell, and then applying from the power supply a pulsed voltage curve which sustains the plasma at a predetermined energy level. The plasma comprises a plurality of high-energy inert gas atoms, a plurality of ions, and a plurality of free electrons. The method then comprises emitting the high-energy inert gas atoms from the plasma cell and cutting, cauterizing, or evaporating the portion of body tissue, or a combination thereof, using the high-energy inert gas atoms. The method may comprise emitting only the plurality of high-energy atoms, and essentially none of the pluralities of ions or electrons from the apparatus.

Where the method comprises creating an incision in the portion of body tissue or evaporating a portion of tissue, the method may further comprise simultaneously creating a cyst wall of cauterized tissue surrounding the incision or evaporated tissue. The method may be performed with at least a portion of the hand-piece tip submerged underwater. The method may be used for general surgery, micro-surgery, endoscopic surgery, and laparoscopic surgery, and on tissues including but not limited to bones, cartilage, liver, lung, stomach, intestines, brain, muscle, and skin tissues.

BRIEF DESCRIPTION OF DRAWINGS

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures:

FIG. 4B is applied through an inductance coil.

DETAILED DESCRIPTION OF INVENTION

Figures 1A, 1B:
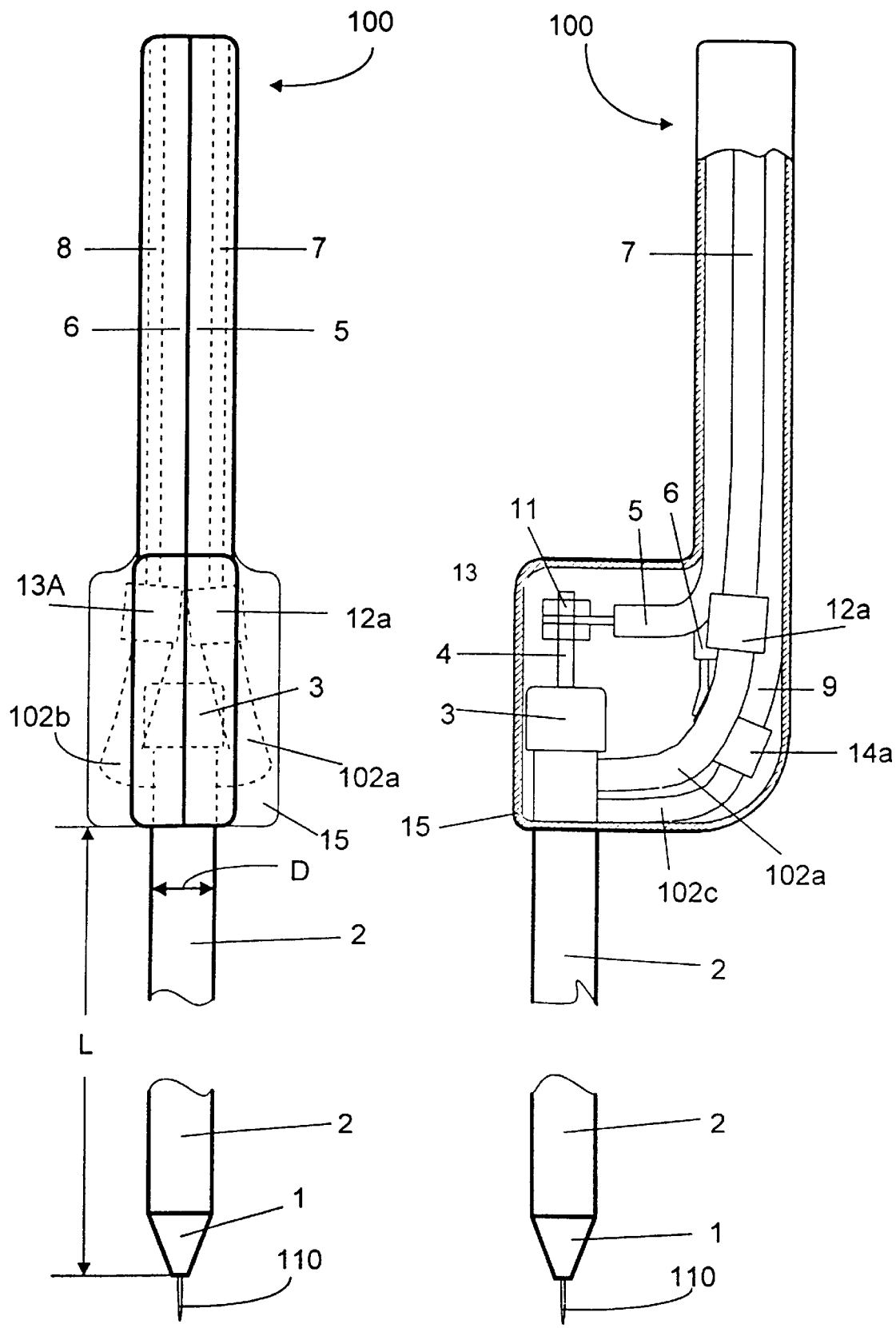
FIG. 1A shows a front view of an exemplary hand-piece and hand-piece cover, with the water circulation connections to the hand-piece body inside the cover shown in dashed lines.
FIG. 1B shows a side view of the hand-piece and cover of FIG. 1A, with the cover partially cut away to show the electrical, water, and gas connections to the hand-piece body.

Before discussing in detail the apparatus of the present invention, it is useful to understand what occurs when a high-kinetic-energy atom, such as is generated and emitted by the apparatus of the present invention, hits a bio-molecule. For consistency, all types of energy, such as chemical binding energy, electrical energy, kinetic energy, or the temperature equivalent of these energies, are expressed as "per particle energy" or "quantum energy."

Chemical binding energy $\Delta E_{Ch}$(KJ/mole), can be expressed per molecule energy (quantum molecular energy) by dividing by Avogadro number:

$$dE_{Ch} \text{ (J/molecule)} = \frac{1000 * \Delta E_{Ch} \text{ (KJ/mole)}}{6.022 * 10^{23}} \tag{1}$$

Joule/molecule energy can be expressed as electron*Volt/molecule energy:

$$1(\text{electron*Volt/molecule}) = 1.6022 * 10^{-19} \text{Coulomb*1Volt/molecule}$$

or:

$$1(\text{e*V/molecule}) = 1.6022 * 10^{-9} \text{(J/molecule)} \tag{2}$$

Using equations 1 and 2, above, molecular chemical binding energy can therefore be expressed in electron volts (eV):

$$\frac{1000 * \Delta E_{Ch} \text{ (KJ/mole)}}{6.022 * 10^{23}} * \frac{1}{1.6022 * 10^{-19}} = dE_{Ch} \text{ (e*V/molecule)} \tag{3}$$

$$dE_{Ch}(\text{e*V/molecule}) = 0.01036 * \Delta E_{Ch}(\text{KJ/mole}) \tag{3}$$

Equation 3 shows that a chemical binding energy with a value of 100 KJ/mole is only equal to 1.04 eV energy. Thus, an electron or single-valued ion should achieve this energy running in an electric field with a voltage of only 1.04 Volts.

Particle energy per molecule can be expressed as temperature (in Kelvin):

$$dE_{Ch} \text{ (J/molecule)} = 3/2 * k * T = \frac{1000 * \Delta E_{Ch} \text{ (KJ/mole)}}{6.022 * 10^{23}}$$

Substituting the value of k (Boltzmann constant, which is equal to $k=1.38*10^{-23}$J/K), the temperature is calculated to be:

$$T \text{ (K)} = \frac{1000 * \Delta E_{Ch} \text{ (KJ/mole)}}{6.022 * 10^{23} * 1.38 * 10^{-23}} * 2/3 = 80.2 * \Delta E_{Ch} \text{ (KJ/mole)} \tag{4}$$

Combining Equations 3 and 4, results in:

$$T \text{ (K)} = 80.2 * \frac{dE_{Ch} \text{ (e*V/molecule)}}{0.01036} = 7,740 * dE_{Ch} \text{ (e*V/molecule)} \tag{5}$$

Equation 5 can be rewritten as:

$$dE_{Ch}(\text{e*V/molecule}) = 1.292 * 10^{-4} * T(K) \tag{6}$$

Using Equation 4, a chemical binding energy of 100 KJ/mole corresponds to approximately 8000 K, which is a relatively high temperature. Thus, breaking bio-molecules with a sub-molecular binding energy of 100 KJ/mole into sub-molecules requires atoms having a temperature of 8000 K, which is equivalent to the energy of an electron or single valued ion moving through an electrical field with a potential of only 1.04 Volts.

The wavelength of the photons issued by the atoms, which indicates the quantum energy, can be calculated as follows:

$$dE = 3/2 * k * T = h * f,$$

where $\lambda = c/f$ and h is Planck's constant ($6.626*10^{-34}$). Thus:

$$3/2 * k * T = h * c / \lambda \rightarrow \lambda \text{ (m)} = \tag{7}$$

$$2/3 * \frac{h*c}{k*T} = 2/3 * \frac{6.626*10^{-34} * 3*10^8}{1.38*10^{-23} * T \text{ (K)}} = \frac{9.603*10^{-3}}{T \text{ (K)}}$$

$$\lambda \text{ (}\mu\text{m)} = \frac{9.603*10^3}{T \text{ (K)}}$$

Equation 7 can be used to calculate the wavelengths of photons corresponding to the kinetic energies or the temperatures of the atoms, and equation 6 can be used to calculate the corresponding energy in electron volts, as shown in Table 1, below.

TABLE 1

| TEMPERATURE (K) | WAVELENGTH (μM) | ENERGY (eV) |
|---|---|---|
| 2,000 | 4.80 | 0.26 |
| 5,000 | 1.92 | 0.65 |
| 12,000 | 0.80 | 1.55 |
| 24,000 | 0.40 | 3.10 |
| 30,000 | 0.32 | 3.88 |
| 35,000 | 0.27 | 4.52 |

Table 1 shows that a temperature of 12,000 K corresponds to red visible light, whereas a temperature of 24,000 K corresponds to violet visible light. Atoms having the above temperatures issue photons having the above wavelengths, thus making it possible to approximate the temperatures of the atoms by looking at the color of the atom beam. Temperatures below 12,000 K can be measured with an infrared-measuring device.

Macro bio-molecules are built from smaller molecules, such as amino acids, nucleotides, fatty acids, and the like. The binding energies between these molecules are below the standard adenosine triphosphate (ATP) hydrolysis energy of 7.3 Kcal/mole which is utilized in the production process of these molecules. Using equations 3 and 4, the standard ATP hydrolysis energy can be expressed in other units:

$$dE_{Ch}(e*V/molecule)=0.01036*4.186*7.3=0.32 \qquad (8)$$

$$T(K)=80.2*4.186*7.3=2,450 \qquad (9)$$

To break the amino acids, fatty acids, and nucleotides into still smaller molecules that can evaporate easily, larger energies are required. Average bonding energies for various chemical bonds common in organic material, expressed in KJ/mole and corresponding temperature are shown in Table 2 below:

TABLE 2

| BOND | ENERGY (KJ/MOLE) | TEMPERATURE (K) |
|---|---|---|
| C—N | 292 | 23,420 |
| C—C | 348 | 27,910 |
| C—O | 356 | 28,550 |
| C—H | 415 | 33,280 |
| O—H | 463 | 37,130 |

Figure 2:
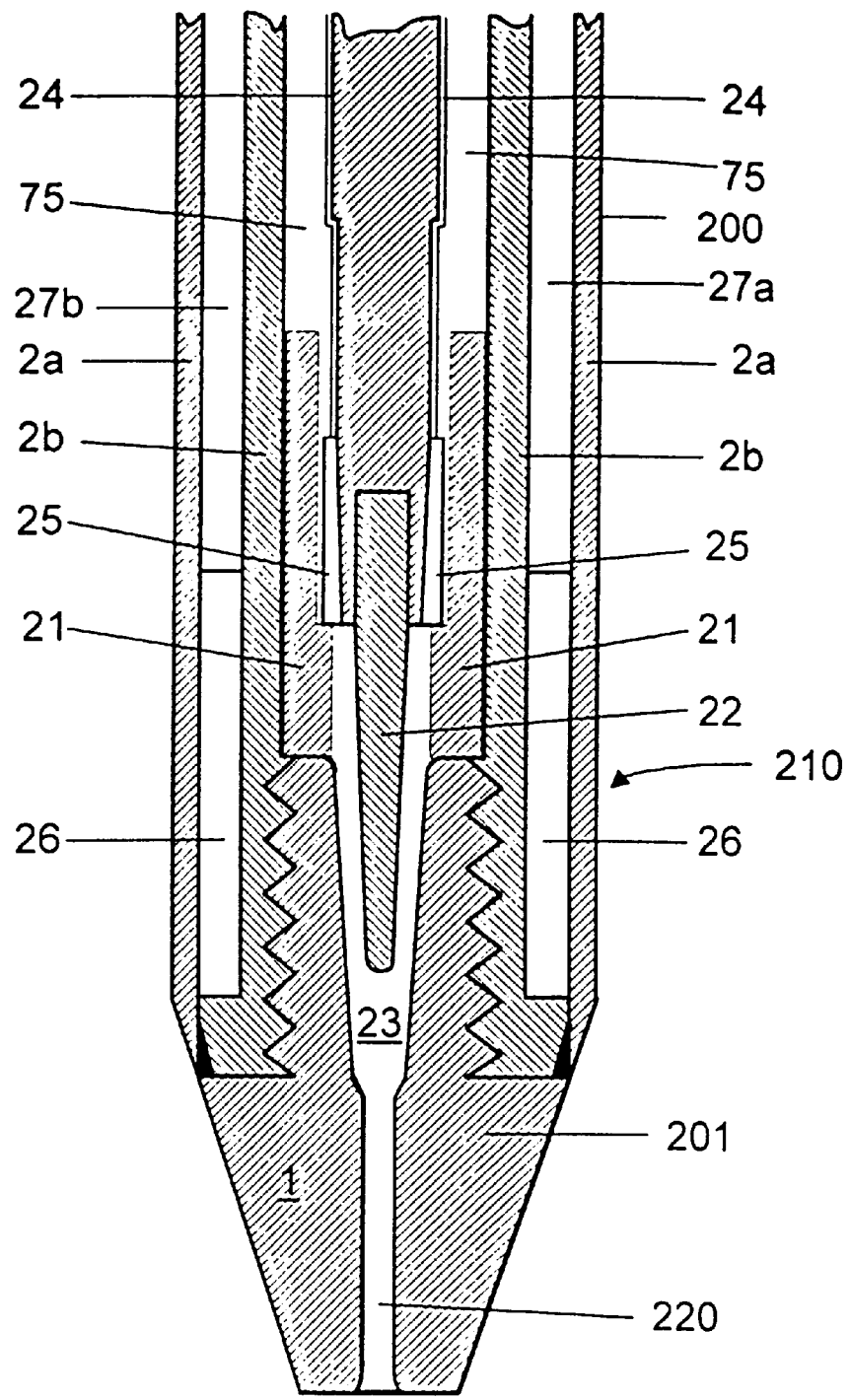
FIG. 2 shows a longitudinal section view of a proximal portion of an exemplary hand-piece body.

As an overview of the process that is integral to the apparatus of the present invention, referring now to FIG. 2, inert gas atoms are energized in plasma cell 23, which is bounded in part by tip 201 of hand-piece 200, which is biased to ground. Initially, electrons generated by negative electrode 22 hit inert gas atoms in plasma cell 23 and liberate one or more electrons from the outer electron shell of the inert gas, thereby converting the inert gas atoms into positive ions. The positive ions move in the applied electrical field towards the negative pole (electrode 22) and the electrons move towards the positive pole (tip 201), thereby converting electrical field energy to kinetic energy in these moving ions and electrons. In turn, these ions and electrons lose their kinetic energies to other inert gas atoms that they hit during their respective movement toward the negative and positive poles. When the ions finally reach the negative pole, they receive electrons from the negative pole and are converted to atoms again. The electrons are transferred to the power source when they reach the positive pole.

Just as electrons fed into the plasma cell create ions when they collide with atoms, electrons released during the ionization process collide with other atoms to create additional ions, creating a chain reaction. The inert gas undergoing such a chain reaction process is known as a "plasma." Plasma has a negative resistance, meaning that it grows by itself due to a chain reaction as long as the starting parameters are kept constant. The apparatus of the present invention controls critical parameters so that the total energy of the plasma, the quantum energy of the individual particles in the plasma, and the energy lost to the metal body are controlled and predictable.

In plasma cell 23, the quantum energy of some of the individual particles is very high, on average about 50,000 K. Atoms energized in plasma cell 23 are guided through channel 220 so that they are emitted from tip 201 at the desired quantum energy level. The geometry of channel 220 affects the quantum energy level. As the atoms hit electrode 22 and the walls of channel 220, they heat these components, and similarly heat any components that they contact. The present invention cools the walls and other components effectively so the metal body temperature and the components' temperatures are kept sufficiently low to allow hand-held use of the apparatus.

The invention is illustrated in detail with reference to the figures wherein similar numbers indicate the same elements in all figures. Such figures are intended to be illustrative rather than limiting and are included herewith to facilitate the explanation of the apparatus of the present invention.

Referring now to FIGS. 1A–16, there are shown the various components and interchangeable hand-pieces of an exemplary surgical instrument of the present invention for generating a plasma from which high energy atoms are emitted from the tip of the instrument for cutting, cauterizing, sterilizing, and evaporating tissue. FIG. 5 provides a block diagram illustrating the basic components of an exemplary apparatus of the present invention, and FIGS. 12A and 12B illustrate a typical physical embodiment of apparatus 1200. Main cabinet 40 of apparatus 1200 preferably comprises a double box system with an upper box 40a mounted on a lower box 40b. Cooling water tank 50, cooling water pump 51, cooling control 52, and gas control system 49 (shown in FIG. 5) are typically housed in lower box 40b. Gas container 48, such as a 5-liter Argon gas container, can typically be placed at or near the bottom, or larger gas containers may be placed separately and connected to gas control system 49.

Pulsative DC power supply 41, impulse voltage source 42, programmable logic controller (PLC) 43, control panel 44, and secondary electrical systems 46 are typically mounted in upper box 40a. Foot pedal control 45 may be connected to cabinet 40. Cables of cabinet cable and tube system 53 are connected to upper box 40a, while the tubes are connected to lower box 40b. Cable and tube system 53 may have at least two preferable configurations: (1) hanging above cabinet 40, adjustable in the X, Y, and Z directions, as shown in FIG. 12B, and weight counter-balanced, or (2) lying on the floor rising up beside the operation table (not shown). As shown in FIG. 12B, rotation about bearing 1250 along arrow S and 360° pivoting at point P allow movement in the X-Y plane and pivoting about pin 1260 along arrow T allows movement in the Z plane within the range of movement permitted by stops 1262 and 1264. Counterbalance 1266 is adjustable along arrow W to provide the degree of counterbalancing desired. Cabinet 40 preferably has wheels 1202, as shown in FIG. 12A, to make it mobile in operation rooms.

As shown by the interconnected lines in FIG. 5, PLC 43 controls all basic functions of apparatus 500. PLC 43 defines the logic of the system. Interlocks may be programmed to prevent the apparatus from starting if certain measured values are not within a desired range. If during use of the apparatus, certain parameters reach unacceptable values, PLC 43 may shut down the apparatus safely in accordance with the defined logic. PLC 43 also may calculate the amount of the current (or the energy) needed for each value of gas flow provided in response to the operator pressing the "energy up" or "energy down" switch using control panel 44 or foot pedal 45. Such calculation may be performed using preset curves built into the PLC software. There are preferably at least five such curves in the software, each of which can be chosen by pressing on one of the quantum energy switches on control panel 44 (shown in FIG. 13 and described in more detail below). Each curve is defined to provide the electrical power needed for each gas pressure or gas flow measurement to keep the quantum energy of the atoms constant. Thus, a high quantum energy curve would provide a relatively higher electrical power at a given measured gas pressure or gas flow than a lower energy curve would provide for the same given gas measurement.

Figure 13:
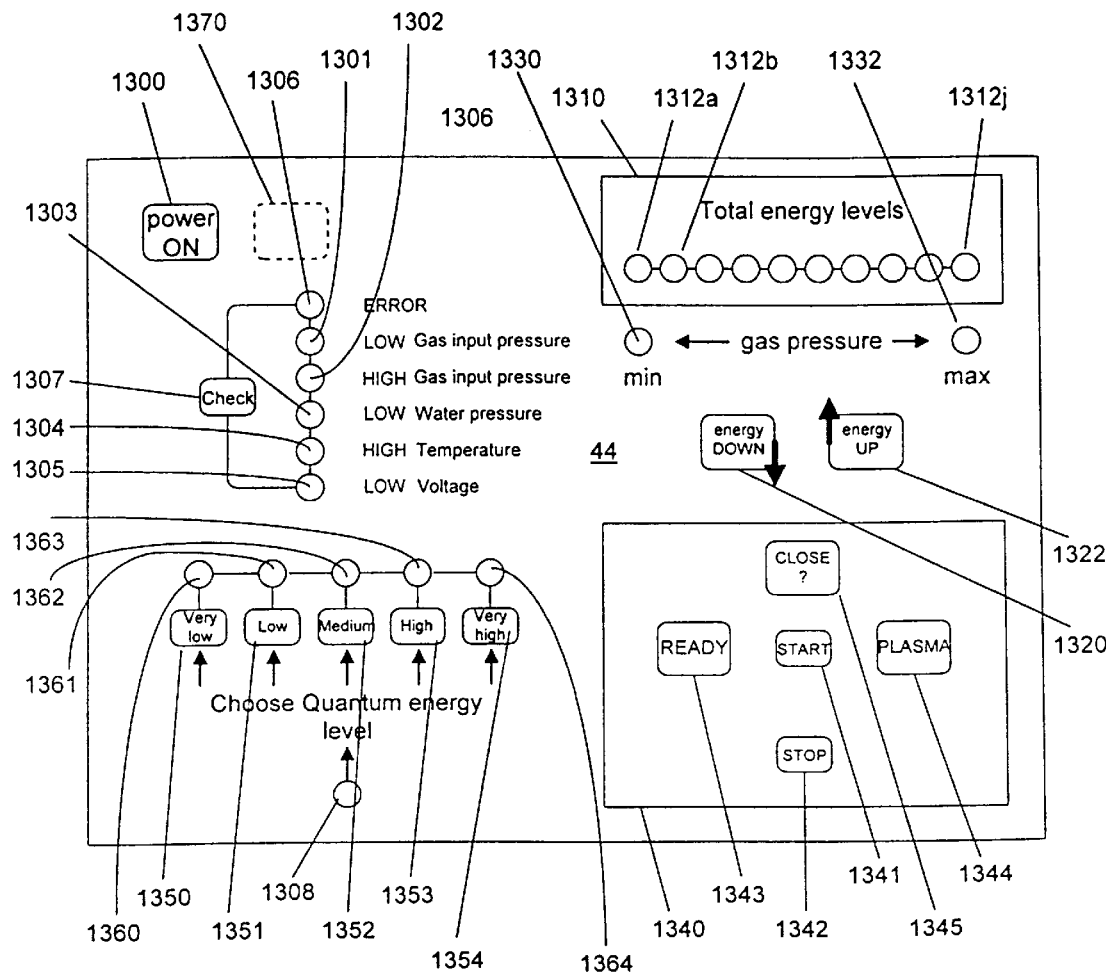
FIG. 13 is an illustration of an exemplary control panel according to the invention.

Control panel 44, as shown in FIG. 13, typically contains a number of switches, including power-on switch 1300, and indicators, such as in the form of lights that are illuminated to indicate if certain parameters are not correct or to indicate system status. For example, indicator 1301 may light if gas input pressure is too low or indicator 1302 may light if the pressure too high. Indicator 1303 shows if the water circulation pressure is too low, indicator 1304 lights if the apparatus temperature is too high, and indicator 1305 illuminates if the voltage is too low. Error indicator 1306 may indicate that one of the above out-of-range parameters or some other software interlock has stopped the use of the system or shut the system down. Other indicators showing the status of other parameters may also be present. Before the equipment is started, various parameters can be checked by pressing check switch 1307. Instead of alarm indicators or "dummy lights," the control panel may instead contain readouts of all the critical parameters for continued monitoring, or a combination of readouts and alarm indicators. There may be a separate power-on indicator 1370, or power switch 1300 itself may illuminate when the system is on, or both. When all of the critical parameters are within the operating range, PLC system 43 lights indicator 1308 to indicate that the operator may proceed to choose a quantum energy level.

The desired quantum energy or power level may be chosen by depressing one of the energy levels switches: very low (1350), low (1351), medium (1352), high (1353), and very high (1354), which are typically so labeled for easy identification by the user, as shown in FIG. 13. Although five quantum energy levels are shown herein, there may be more or fewer levels. An indicator light 1360–1364 corresponds to each switch, as shown in FIG. 13. Using these switches, atomic temperatures between approximately 5000–20,000 K may be achieved, as desired. The atomic temperature ranges corresponding to each quantum energy level are shown in Table 3 for a typical relatively low-energy apparatus.

TABLE 3

| QUANTUM ENERGY SETTING | ATOMIC TEMPERATURE |
|---|---|
| Very Low | 2,000 |
| Low | 5,000 |
| Medium | 10,000 |

TABLE 3-continued

| QUANTUM ENERGY SETTING | ATOMIC TEMPERATURE |
|---|---|
| High | 15,000 |
| Very High | 20,000 |

Readout 1310 indicates the total energy continuously using a color code, where each indicator 1312 illuminates with a different color along a continuum from red at 1312a to violet at 1312j. The total energy level may be adjustable using "energy down" switch 1320 and "energy up " switch 1322 on control panel 44 and/or foot pedal control 45 (shown in FIGS. 5 and 12). Indicator 1330 indicates if the gas outlet pressure is at a minimum and indicator 1332 indicates if the gas outlet pressure is a maximum allowable level. PLC 43 may further contain an interlock to prevent an increase or decrease in energy if such a change would cause the apparatus to exceed one or more of the allowable operating parameters, such as the energy level, gas pressure, or any of the parameters indicated by indicators 1301–1305. When energy down switch 1320 is interlocked by PLC 43, it may be unlocked by pressing energy up switch 1322. Conversely, an interlocked energy up switch 1322 may be unlocked by pressing energy down switch 1320.

Block 1340 includes start switch 1341 and stop switch 1342, as well as three indicators: "ready" indicator 1343, "plasma" indicator 1344, and "close?" indicator 1345. When all input parameters are correct and the quantum energy level is chosen, "ready" indicator 1343 is on and start switch 1341 may be pressed to start plasma generation. When the transition period leading to a stable plasma is complete, the "plasma" indicator 1344 is illuminated. If the operator does not make any inputs or otherwise exert some control on the equipment for a predetermined time period, "close?" indicator 1345 illuminates, and an alarm signal may additional 14 be sounded. If the operator takes no action within an additional predetermined time period, the equipment shuts itself down. Start and stop controls may also be present in foot pedal control 45.

Foot pedal control 45 has at least four switches that are very clearly distinguished, for start (1341F), stop (1342F), energy down (1320F), and energy up (1322F). As shown in FIG. 12A, the operator places one foot on recessed area 1220 of foot pedal 45 on swinging plate 1222 which pivots about pin 1223 and under which switches 1320F and 1322F are positioned, so that slightly moving his or her foot to the left or right activates the corresponding switch. The operator then may lift his or her foot higher to reach switches 1341F and 1342F on raised areas 1224 of foot pedal 45 to start or stop the equipment. After the operator chooses a quantum energy level, he or she can control the equipment with the foot pedal alone, if desired. Foot pedal control 45 is connected to cable 1210 that supplies electrical voltage to the switches in the foot pedal and transmits the output of the switches back to PLC 43. The opposite end of cable 1210 may have any connector (not shown) known in the art for providing a quick connection to the back wall of upper box 40a of apparatus cabinet 40.

Secondary electrical systems 46 (shown in FIG. 5) include various low voltage power supplies and relay systems needed to coordinate the different sub-systems of the apparatus, as are commonly known in the art for performing such tasks.

Figure 16:
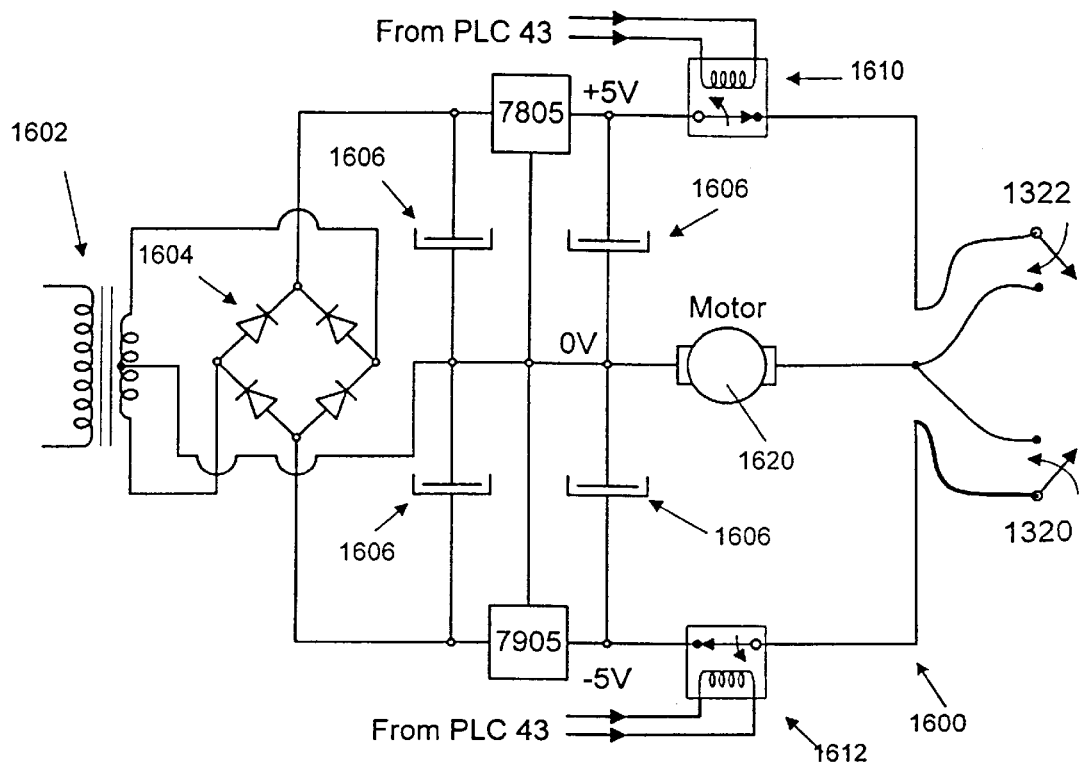
FIG. 16 is a schematic diagram illustrating an exemplary circuit for increasing or decreasing gas flow.

Gas container 48 may typically have a mechanical pressure adjustment control and a high-pressure indicator. The output pressure of gas container 48 is typically adjusted to about 8 atmospheres as the input pressure to the apparatus. Gas control system 49 comprises a standard mechanical regulator, such as a model LRP-1/4-0.7 (having a range of 0–700 Torr over about 15 turns of the regulator), manufactured by FESTO of Germany. The mechanical regulator is driven by an actuator to increase or decrease the pressure or flow of the gas through the regulator. A low-speed electric DC motor, such as a 6-volt 1.61.013.306-8 "F" manufactured by Bühler of Nürnberg, Germany having a rotation speed of about 20 RPM may be used as the actuator. Control circuit 1600 as shown in FIG. 16 may be used to control the motor/regulator combination. Other actuators and actuation mechanisms, however, may be used to automatically regulate the gas flow as are known in the art.

As shown in FIG. 16, control circuit 1600 comprises a transformer 1602, a diode bridge 1604, a number of capacitors 1606, voltage stabilizer transistors 7805 and 7905, relays 1610 and 1612 connected to PLC 43, motor 1620, and energy up and energy down switches 1320 and 1322, respectively. Voltage stabilizer transistor 7805 stabilizes the voltage to +5 Volts, while transistor stabilizer 7905 stabilizes the voltage to −5 Volts. Activation of "energy down" switch 1320 or "energy up" switch 1322 on control panel 44 or like switches on foot pedal control 45 complete the respective circuits to energize the motor to rotate in one direction or the other. "Energy up" rotates the motor to turn the actuator to increase the gas flow, whereas "energy down" rotates the motor to turn the actuator to decrease the gas flow. Gas control system 49 may further comprise a pressure or flow sensor (not shown) to measure the actual pressure or flow. A signal from the pressure sensor may be connected to PLC 43, which may activate relay 1610, preventing rotation of the motor to further open the gas valve if the pressure is too high, or relay 1612, preventing rotation of the motor to further close the gas valve if the pressure is too low. Although shown schematically in FIG. 16 with relays, the same functionality may also be provided via software. Gas control system 49 may also have other hardware limits for the maximum and minimum gas pressure or flow levels.

Cooling water tank 50 supplies water to cool hand-piece 47, as shown in FIG. 5. The cooling water system is a closed circulation system, but the water is typically sterilized and/or contains sterilization agents to protect contamination of the body tissues in the event of leakage. The cooling channels are preferably all welded to minimize the potential for leaks. Cooling water pump 51 is a circulation pump that typically begins functioning as soon as the power switch is put on. Cooling control sensor 52 comprises a flow or pressure sensor that senses if the water circulation or water pressure is a predetermined amount or greater. If the circulation or pressure is below the predetermined amount, sensor 52 sends a voltage signal to PLC 43, which prevents operation of the apparatus. If this happens while the apparatus is functioning, PLC 43 immediately initiates a shut down sequence. The sequence typically comprises first shutting off electrical power and then turning off gas flow after the electrode cools. This sequence allows the continued inert gas flow to cool the electrode, thus protecting the negative electrode against increased oxidation rates at high temperature by keeping out oxygen until the electrode is cool.

Cabinet cable and tube system 53 comprise inert gas and cooling water tubes which are connected to lower box 40b and power cables which are connected to upper box 40a of cabinet 40. Where a cable hanging system is used such as is shown in FIGS. 12A and 12B, the tubes and cables are contained within a shaped conduit 53, preferably aluminum, that is connected to apparatus cabinet 40. The shaped conduit is preferably weight balanced, as is known in the art for similar medical equipment, so that hand-piece 47 can be moved up, down, and laterally with ease without feeling the weight of the system. Where a floor-type cable system is used, all tubes and cables go through a conduit that extends upwardly beside the operator. Cabinet cable and tube system 53 may preferably be connected to hand-piece cable and tube system 55 via a quick connect 54, which may comprise a number of individual quick connects, one for each tube or cable, or may be an integrated device allowing quick connection of all cables and tubes simultaneously. The detail of such individual or integrated quick connects may be similar to any such devices generally known to those skilled in the art. Cabinet cable and tube system 53 is connected to element 54a of quick connect 54, whereas hand-piece cable and tube system 55 is connected to mating element 54b of the quick connect. Hand-piece 47, along with cable and tube system 55 and quick connect element 54b, can be sterilized thermally or chemically as a unit, as required, before each operative procedure. The selection of the components of hand-piece 47, cable and tube system 55, and quick connect element 54b, such as insulation material of the cables, gas or water tubes, connectors, gaskets, and the like, are therefore chosen to withstand such sterilization.

There are at least two types of preferable pulsative DC power supplies 41. One such power supply is adapted to create the voltage curve shown in FIG. 4A. This type of power supply is used for high-energy applications such as liver surgery or orthopaedic surgery. For the curve shown in FIG. 4A, rectangular-shaped voltage pulses are added on top of a constant DC voltage. The second type of power supply creates the voltage shape shown in FIG. 4B. This type of power supply can be used for high, medium, low and very low energy micro-surgical applications such as brain surgery. For the curve shown in FIG. 4B, only rectangular shaped voltage pulses are present, without the underlying constant voltage.

There are three time parameters that define the voltage shape: duty period of the rectangular pulse $t_p$; off time of the voltage $t_z$; and total time period of the voltage applied $t_0$. Total time period $t_0$ is equal to duty period $t_p$ plus off time $t_z$. ($t_0 = t_p + t_z$). Inverse of total time $1/t_0$ is equal to frequency of the power supply $f_0$.

Figure 4A:
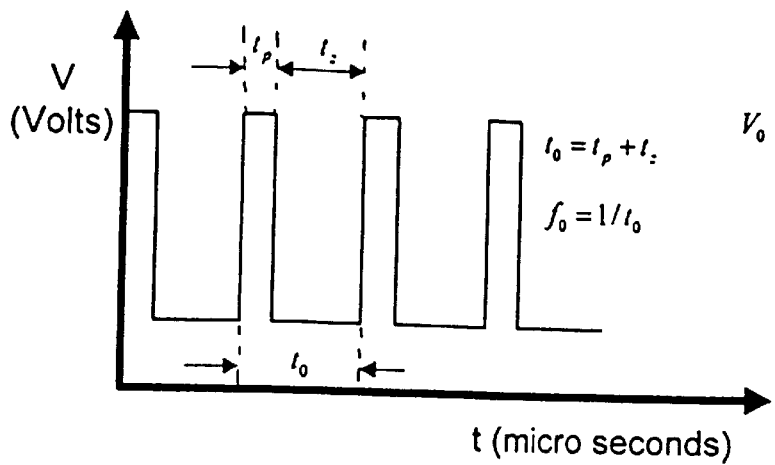
FIG. 4A illustrates a graph of time in microseconds versus volts showing an exemplary voltage curve supplied by the power source of the present invention.
Figure 4B:
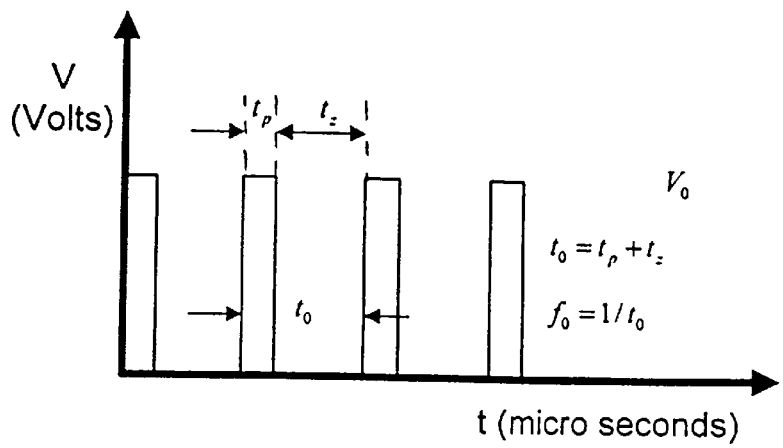
FIG. 4B illustrates a graph of time in microseconds versus volts showing another exemplary voltage curve supplied by the power source of the present invention.
Figure 4C:
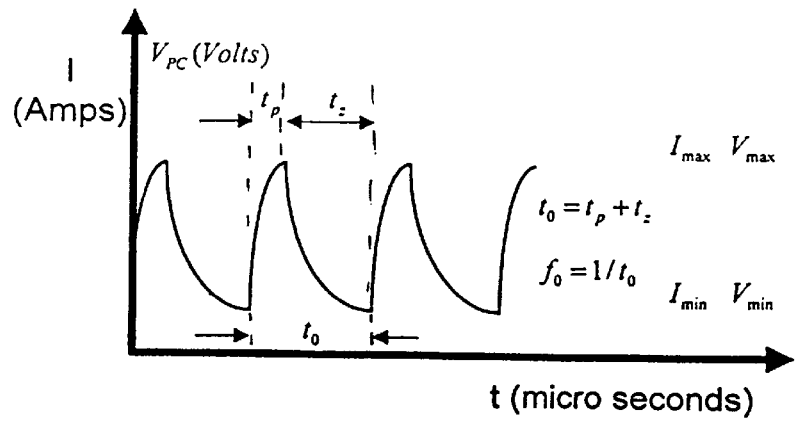
FIG. 4C illustrates a graph of time in microseconds versus amps and volts showing exemplary current and voltage curves obtained at the plasma cell when the voltage curve of FIG. 4A
Figure 5:
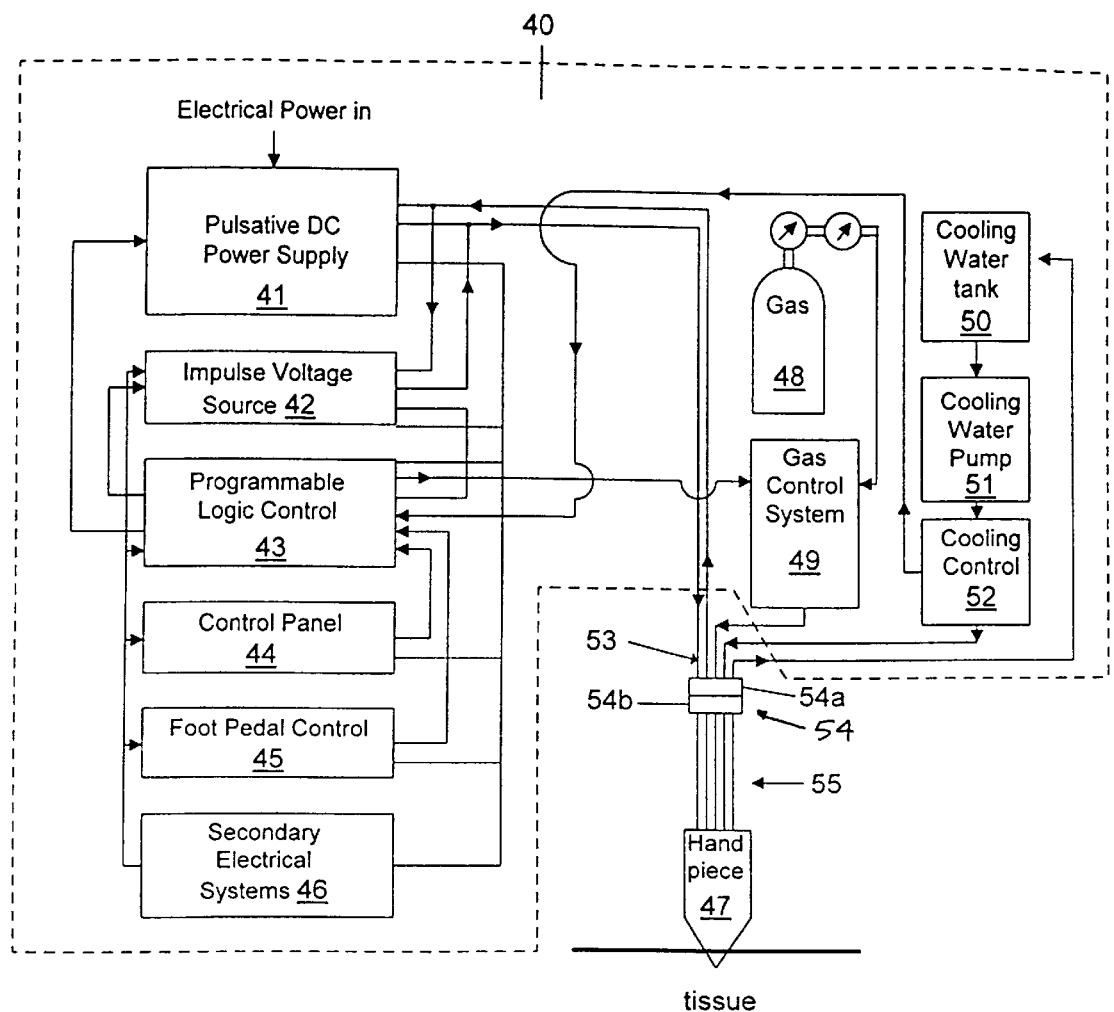
FIG. 5 shows a schematic block diagram of an exemplary system of the present invention.
Figure 14A:
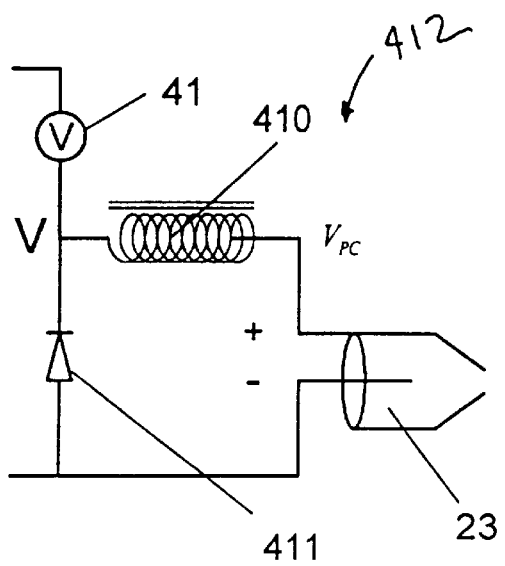
FIG. 14A is a schematic diagram illustrating an exemplary relationship between the voltage source, inductance coil, and plasma cell of the present invention.

The voltage of the DC power supply is applied on the electrodes of the plasma cell through a serial inductance circuit 412 as shown in FIG. 14A, creating a curve such as is shown in FIG. 4C. Inductance circuit 412 comprises an inductance coil 410 and a diode 411 between voltage source 41 and plasma cell 23. Inductance coil 410 supplies the current of the plasma cell, during the period $t_z$ when the power supply has zero voltage. As a result, the sharkfin-shaped plasma current curve in FIG. 4C is obtained. When voltage $V_0$ is applied, the current increases exponentially. The current i decreases exponentially when the voltage drops to zero. The voltage curve corresponding to the current curve has the same sharkfin shape.

Figure 14B:
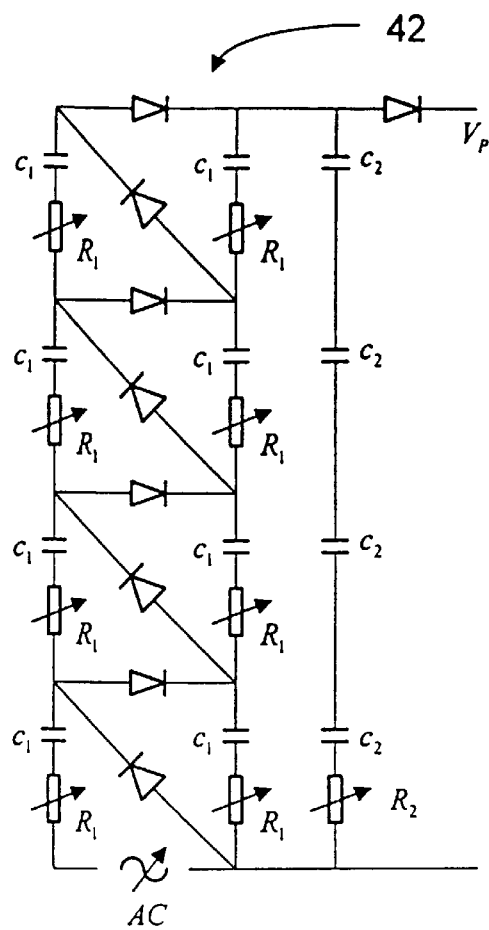
FIG. 14B is a schematic diagram illustrating an exemplary impulse voltage source comprising a voltage multiplier circuit.

The plasma is initiated by impulse voltage source 42, which may be a voltage multiplier circuit as is known in the art, for example as shown in FIG. 14B. The plasma is then maintained by the voltage of pulsative DC power supply 41. To maintain ionization of the argon atoms, a minimum voltage of 15.75 volts is needed, as the ionization energy of the first electron of the argon atoms is 15.75 eV. General technology for increasing gas flow and increasing the total electrical energy using an ordinary DC power supply is well known in the art. Decreasing total energy to very low electrical power levels, such as a hundred watts, tens of watts, or a few watts, with a mere DC power supply, however, is generally not possible because the only way to decrease the current of a DC power source is by decreasing its voltage. When a constant DC voltage somewhat above 15.75 V is applied, ionization of the argon atoms in chain reaction occurs. Because of the negative impedance effect, the ionization continuously grows even if the voltage is kept constant. Larger and larger currents are obtained, until the voltage-drop over the series resistance increases, decreasing the voltage applied on the plasma cell and stopping the growth of the current. To decrease the current, the applied voltage is decreased in small steps. When the voltage decreases below a certain value, suddenly the ionization disappears and plasma activity abruptly ends.

To decrease the total energy to very low levels but keep the quantum energy constant requires a combination of reduced plasma cell dimensions, reduced gas flow, and reduced electrical power. To avoid breaking the plasma ionization chain-reaction at low energy levels, the voltage applied on the positive and negative electrodes in accordance with this invention is not a simple DC voltage, but rather the pulsed DC voltage, as shown in FIGS. 4A and 4B. As shown in FIG. 4C, the ionization voltage peak is applied on the atoms for a limited time, and the current is not allowed to increase, but instead decreases exponentially, until a new peak voltage is applied, when the current is increased again, keeping the needed average value. The peak value of the voltage is enough to ionize the atoms. When the voltage decreases very quickly, the chain reaction of electron creation stops, no new electrons are created, but the electrons already created sustain the current at a lower level. Before the electron transfer ends from one pole to the other, a new voltage peak is applied. This method makes it possible to attain very low power levels. For this purpose, the frequency of up to hundred kilohertz are chosen to use the inertia of the plasma without breaking the chain reaction, where the zero voltage period for the power source $t_z$ is increased while $t_p$ is decreased. The total power level may be adjusted to any level required, for any of the hand-pieces described herein, by changing parameters such as frequency $f_0$, duty period $t_p$, and peak voltage $V_0$ of pulsative DC power supply 41.

Impulse voltage source 42, shown in FIG. 14B, is a voltage multiplier circuit, with adjustable input voltage. The input voltage may be chosen as necessary for each type of operation equipment, such as brain surgery, general surgery, and the like. The necessary voltage output can accordingly be adjusted between a few hundred volts and 1,200 volts (DC). Capacitors C1 and C2 as shown in FIG. 14B used in the voltage multiplier source are chosen in accordance with the energy requirement of each different operation tool. The function of impulse voltage source 42 is to apply high DC voltage between the negative and positive electrodes in the plasma cell for a short time period, to start plasma creation. Programmable logic controller (PLC) 43 may adjust this time period based on the maximum total energy for the apparatus, as influenced by gas flow and hand-piece geometry.

Application of the impulse voltage takes place after supplying the inert gas, preferably argon. A negative voltage applied on negative electrode 22 (shown, for example, in FIG. 2), which is typically a sharp tungsten electrode, creates a corona discharge. Electrons discharged from negative electrode 22 move towards the positive electrode (tip 201, which surrounds the negative electrode), and thereby collide with the inert gas atoms, releasing more electrons from the inert gas, thus generating ions and additional new electrons.

When ionization starts creating new electrons, and the atoms begin absorbing kinetic energy, the voltage level of pulsative DC power supply 41 is then enough to maintain the plasma and it takes over energizing the plasma as impulse voltage source 42 is shut off. The two voltage sources 41 and 42 are typically connected in parallel. Impulse voltage source 42 is typically activated for only a very short time period on the order of about 1 to 5 bursts of millisecond duration over a total time period of about a second, while pulsative power supply 41 operates continuously during operation of the apparatus. Impulse source 42 fires until the chain reaction is created, after which time it is short-circuited by pulsative source 41. This occurs because impulse source 42 and pulsative DC power supply 41 are typically connected in parallel to the plasma cell. Power supply 41 is a relatively low voltage, high-power piece of equipment, and impulse source 42 is a relatively high voltage, very low energy source that charges and keeps its energy on a very small capacitor. The impedance of the plasma cell is very high (almost infinite) before impulse source 42 intitiates ionization within the plasma cell. After ionization is initiated and the chain reaction begins, the impedance of the plasma cell goes down, and power supply 41 can apply its low voltage to the plasma cell to sustain the chain reaction. From then on, a low impedance load (the impedance of the functioning plasma cell) is established, and the voltage of impulse source 42 is unable to increase above the corresponding low voltage in the plasma cell, because the low impedance of the plasma cell short circuits the small capacitor of the impulse source to the voltage level of power supply 41.

Each hand-piece 47 is composed of a number of functional elements. Certain elements are common to all hand-pieces, whereas others are unique to certain hand-piece models or modified depending on the type of hand-piece. Different embodiments of the apparatus may be optimized for the total energy and/or the quantum energy required for the various types of medical procedures and the various lengths, diameters and geometric dimensions of the hand-pieces adapted for different types of tissue. As a result, cabinet 40, impulse voltage source 42, pulsative DC power supply 41, PLC 43 software, and hand-piece 47 may be different for different embodiments.

Referring now to FIGS. 1A and 1B, there are shown multiple views of hand-piece 100, which is typically preferred for general surgery and micro-surgery. Hand-piece 100 has a tip 1 and a body 2. The various components of the body are kept together with a screwed end piece 3, as described below. Negative pole 4 protrudes through end piece 3, and is connected to first cable 5, by means of a connector 11, typically a screw connector. Tubes 102a and 102b are typically copper and are typically welded to body 2. Connectors 12a and 13a typically connect tubes 102a and 102b to water circulation tubes 7 and 8, respectively. Second cable 6 is connected to the positive pole of the pulsative DC power supply 41 (shown schematically in FIG. 5), and is typically welded to one of the copper water tubes 102a or 102b. Thus, the positive pole of the pulsative DC power supply 41 (typically biased to ground) is connected to body 2 of hand-piece 100. Inert gas, typically argon, is supplied into the body of the equipment through the tube 102c, which is also typically copper. Tube 102c is welded to body 2 of hand-piece 100, and connects to tube 9, typically plastic, through connector 14a. Hand-piece cover 15, typically plastic, has two functions: as a cover to protect the internal components, and as a grip for an operator to grasp hand-piece 100. The various components may have different dimensions depending upon the type of hand-pieces. Stream 110 of high-energy atoms is shown being emitted from tip 1.

Figure 7:
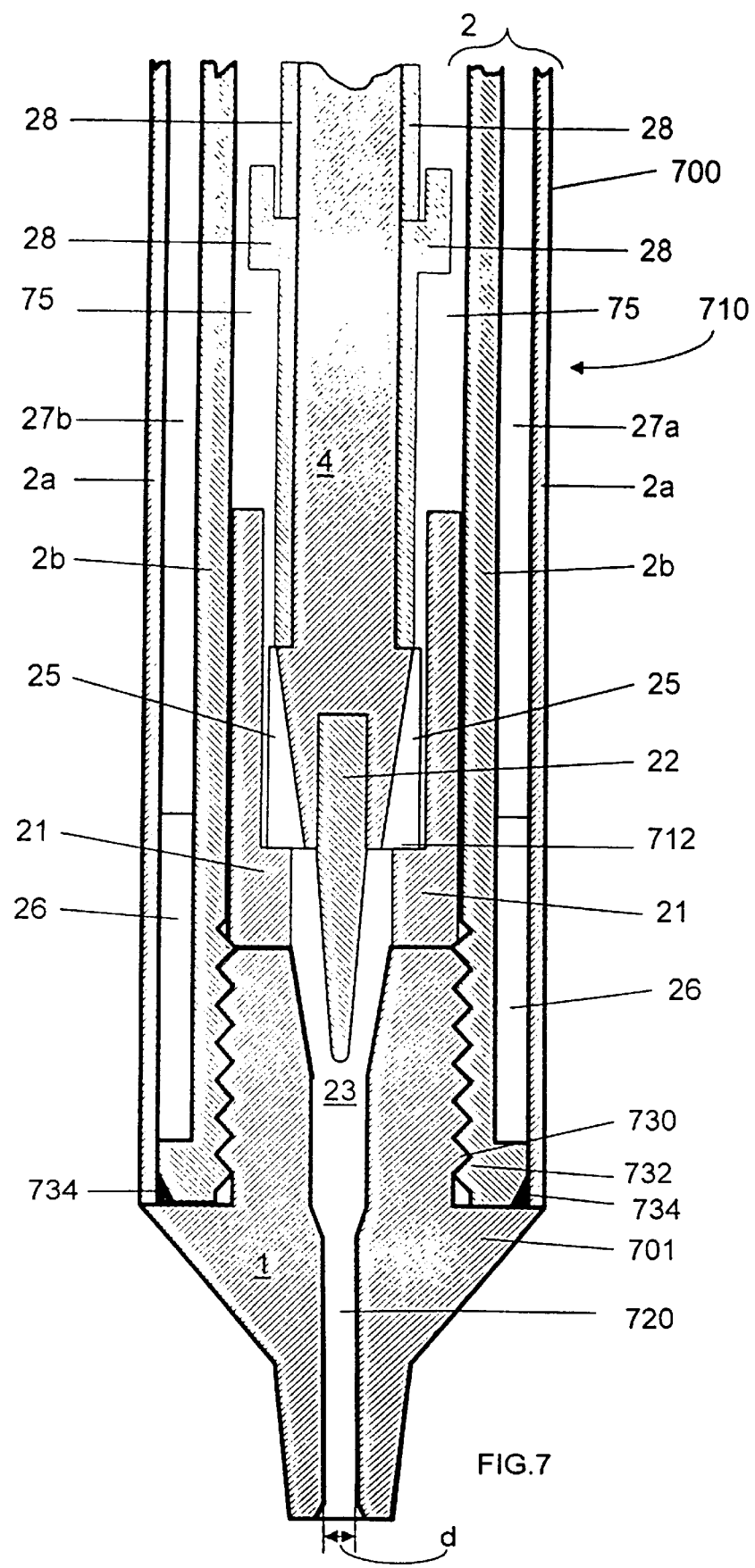
FIG. 7 shows a longitudinal section view of the proximal portion of another exemplary hand-piece body.

FIG. 7 shows the proximal portion 710 of an exemplary hand-piece 700 for use in general surgery. As used herein, the term "proximal" refers to a portion relatively closer to the body being operated upon and the term "distal" refers to a portion relatively further from the body being operated upon. The basic elements described herein with respect to hand-piece 700 are numbered similarly with respect to other hand-pieces described herein. Plasma cell 23 comprises a volume defined by negative pole rod 4, electrode 22 (typically tungsten), insulator 21 (typically ceramic alumina), and hand-piece tip 701. Inert gas enters plasma cell 23 through gas channels 25 within negative pole rod 4 and exits through emission channel 720 in tip 701. Plasma is created and the atoms are energized within the control volume of plasma cell 23. Hand-piece tip 701 is typically fitted with external threads 730 for a screwed connection to internal threads 732 in cylinder body 2.

Negative pole rod 4 conducts negative voltage and electrons to tungsten electrode 22. Because body 2 is electrically connected to the positive pole of the power supply (typically biased to ground), tip 701 is also positively biased to ground. Insulators 28 and 21, typically alumina ceramic, electrically isolate the negative pole rod 4 from body 2. Body 2 comprises an outer cylinder 2a and an inner cylinder 2b, between which are disposed longitudinal water channels 27a and 27b that bring the cooling water to and from circulation channel 26 close to tip 1 around plasma cell 23, to provide cooling. Cylinders 2a and 2b are typically welded together, such as at weld 734.

Figure 11:
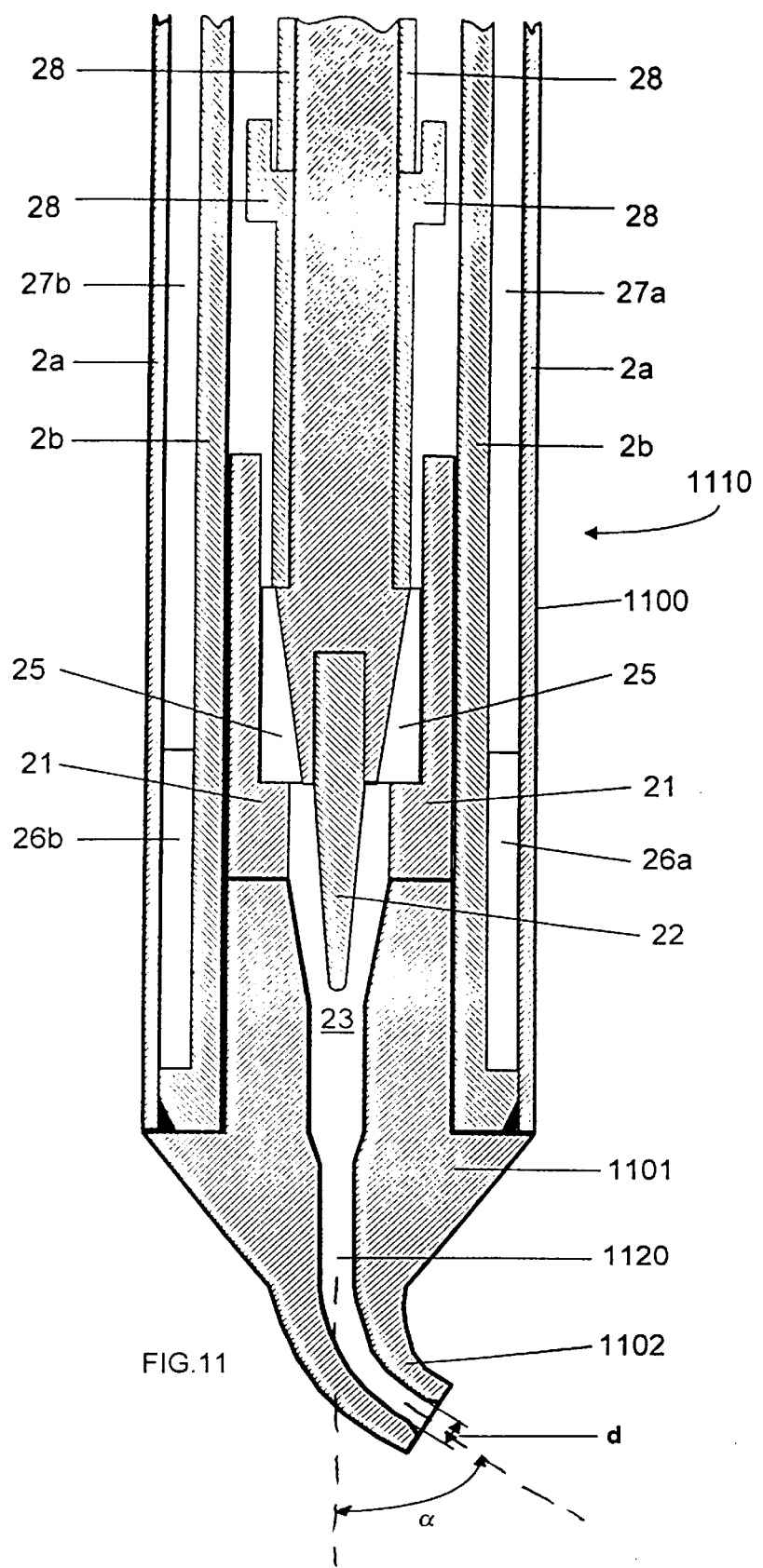
FIG. 11 shows a longitudinal section view of an exemplary hand-piece body similar to that shown in FIG. 7, except having a elongated, curved tip.
Figure 12A:
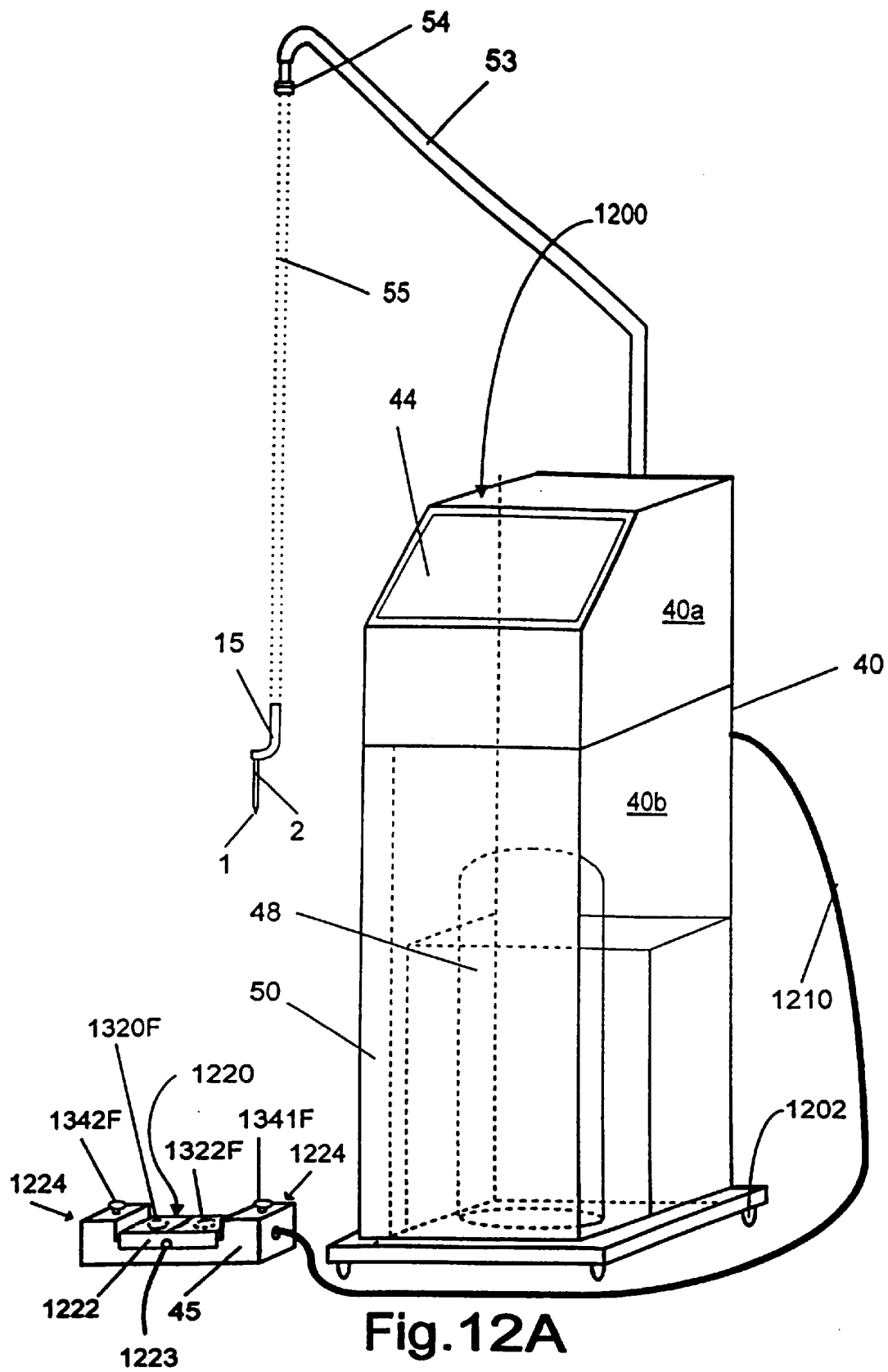
FIG. 12A is a perspective view illustration of an exemplary apparatus according to the invention.
Figure 12B:
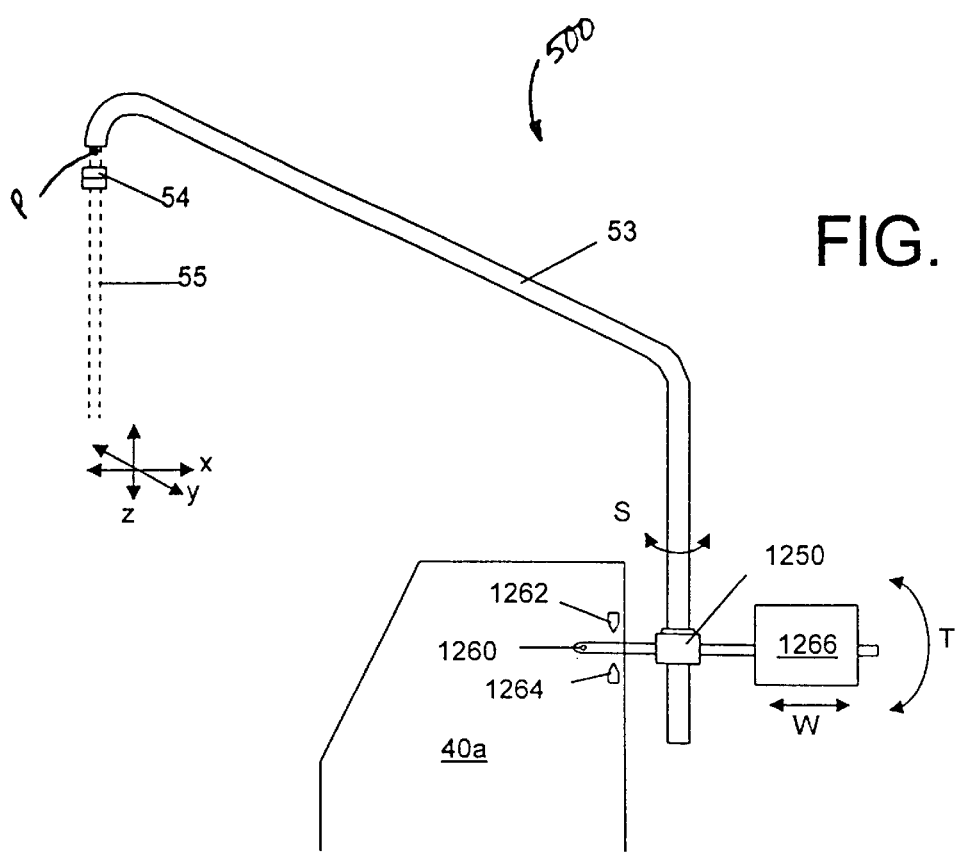
FIG. 12B is a side view illustration of an exemplary counterbalance mechanism of the apparatus shown in FIG. 12A.

FIG. 11 shows a proximal-most portion 1110 of a hand-piece 1100 having a tip 1101 with a curved extension 1102. The proximal portion of hand-piece 1100 is very similar to the proximal portion of hand-piece 700 in FIG. 7, except that tip 1101 has curved extension 1102 and is welded into cylinder body 2 instead of screwed. The curvature of the tip as measured by angle ac may be any curvature desired, such as for example, 30°, 45°, 60°, 75°, 90° or the like. The direction of the curvature in relation to the hand-piece grip may also be important. For example, it can be directed straight ahead, to the left, or to the right, or with some angle to the right or left. A welded connection between tip 1101 and body 2 is preferred for curved tips to set the direction of curvature in relation to the hand-piece grip precisely.

Figure 8A:
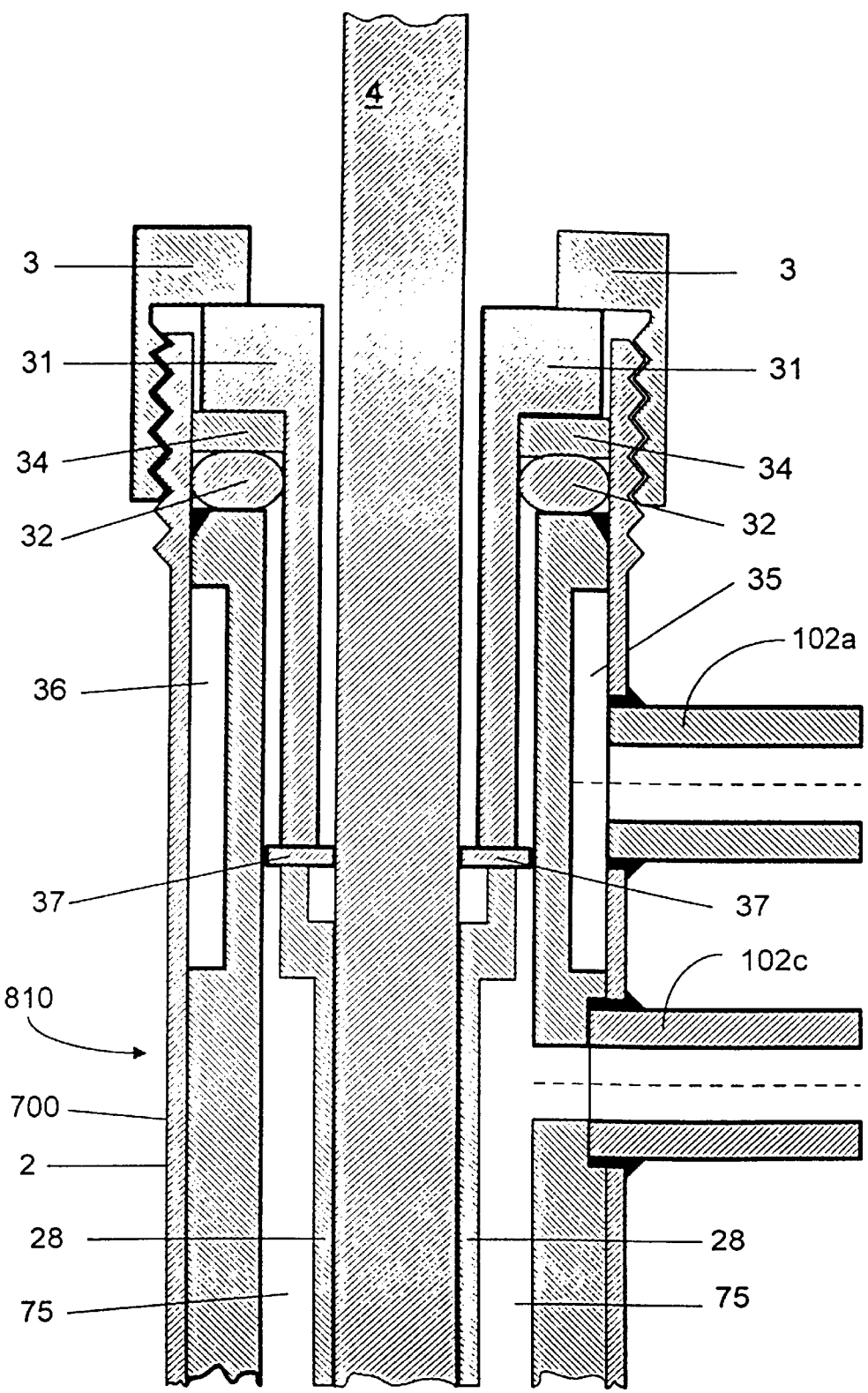
FIG. 8A shows a longitudinal section view of the distal portion of the hand-piece body of FIG. 7.
Figure 8B:
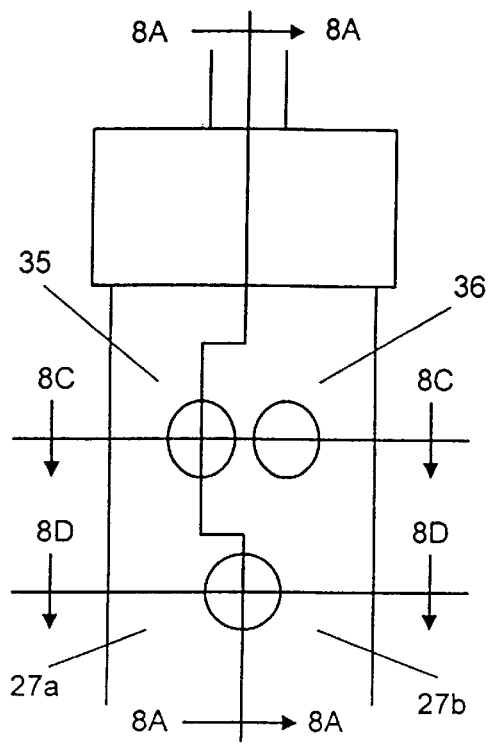
FIG. 8B shows a side view of the distal portion of FIG. 8A, illustrating the longitudinal section lines 8A—8A, 8C—8C, and 8D—8D.
Figure 8C:
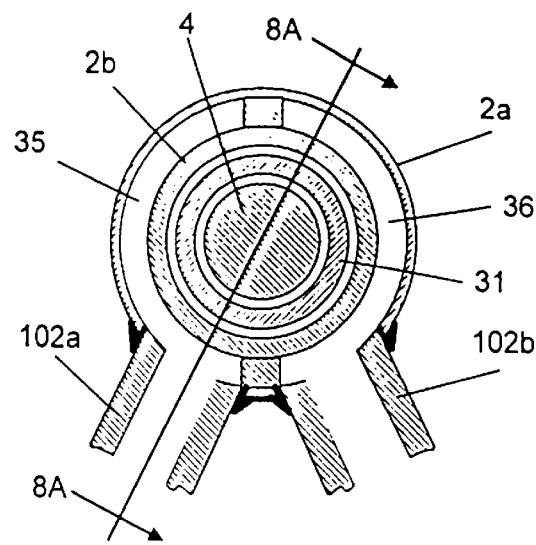
FIG. 8C shows a cross-sectional view of the distal portion of FIG. 8A, taken across line 8C—8C shown in FIG. 8B.
Figure 8D:
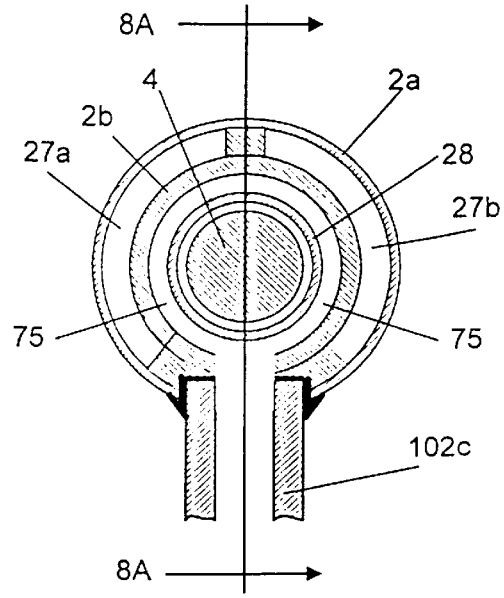
FIG. 8D shows a cross-sectional view of the distal portion of FIG. 8A, taken across line 8D—8D shown in FIG. 8B.

FIG. 8A shows a longitudinal section of distal end 810 of hand-piece 700, taken across lines 8A—8A as shown in the side view of FIG. 8B and in the cross-sectional views of FIGS. 8C and 8D. Negative pole rod 4 protrudes from body 2, isolated by insulators 28 and 31, both of which are typically alumina ceramic, and gasket 37. Gasket 34 and O-ring 32 take up any slack due to production tolerances of the various components as well as prevent gas leakage from the distal end of hand-piece 700. By attaching screwed cover piece 3, compressive force is applied through insulator 31 and gasket 37 and insulator 28 to bottom portion 712 of negative pole rod 4 (shown in FIG. 7) to keep it fixed atop insulator 21.

Inert gas is brought into the hand-piece through tube 102c. Tube 102a brings cooling water into semi-cylindrical channel 35, which is typically nearly a half cylinder (as shown in FIG. 8C), and which guides the water downward to longitudinal inlet channels 27a in body 2 (shown in FIGS. 7 and 8D). The cooling water reaches cylindrical channel 26, makes a half-turn around and returns through longitudinal outlet channels 27b, to reach the other semi-cylindrical channel 36, which is also typically nearly a half cylinder.

The cooling water then exits semi-cylindrical channel 36 through tube 102b.

For micro-surgery applications, such as for the brain or spine, or for arthroscopic or skin surgery, hand-piece 200, a proximal portion 210 of which is shown in FIG. 2, may be preferred. The basic elements of plasma cell 23, negative pole rod 4 including gas channels 25, electrode 22, insulator 21, and tip 1, are similar to those for hand-piece 700 shown in FIG. 7. Unlike hand-piece 700, however, negative pole rod 4 of micro-surgery hand-piece 200 comprises an insulative coating 24, typically alumina ceramic, to isolate the pole rod from body 2, rather than one or more distinct insulator sleeves 28 as present in hand-piece 700.

Figure 6:
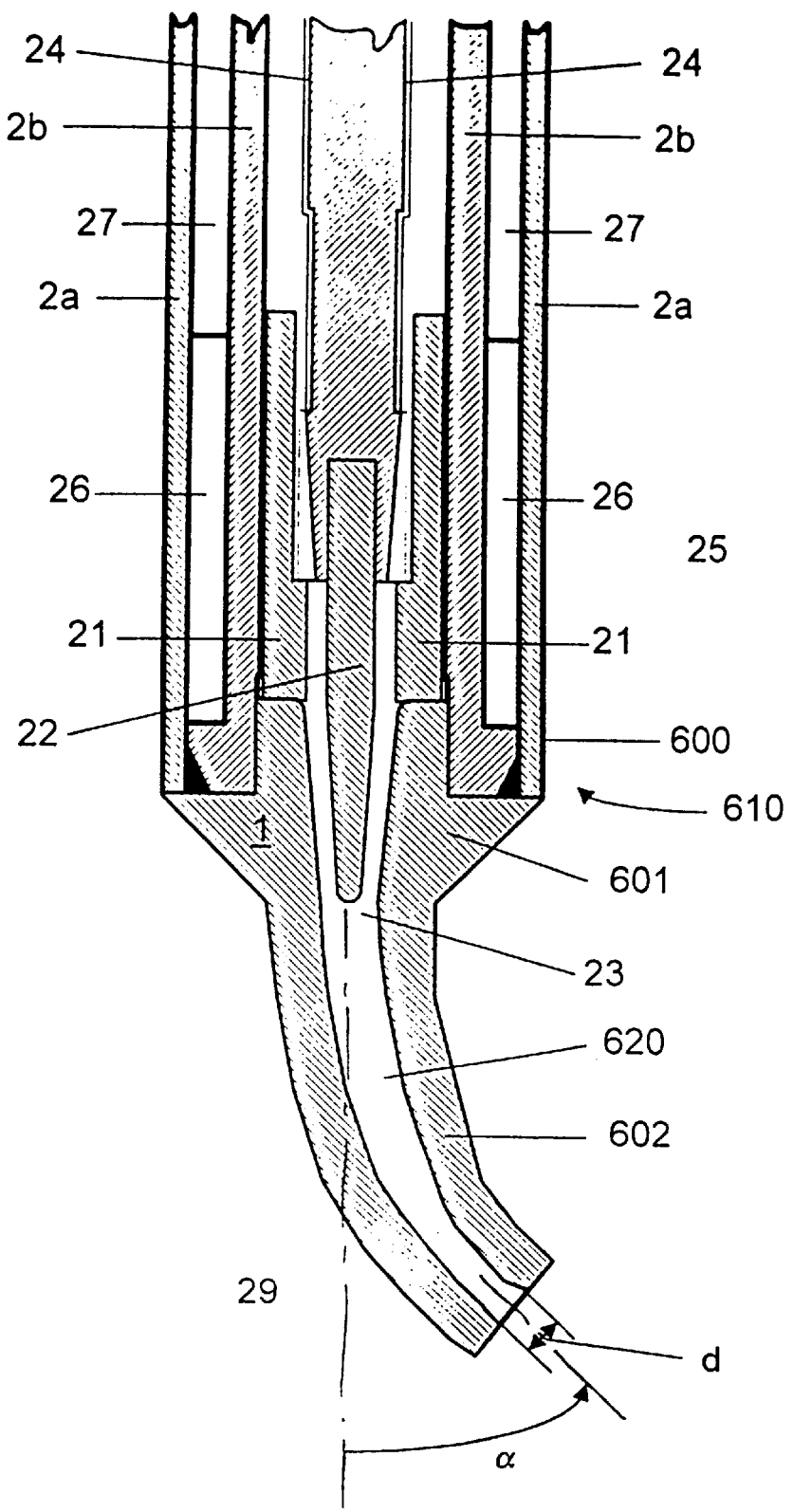
FIG. 6 shows a longitudinal section view of an exemplary hand-piece body similar to that shown in FIG. 2, except having a elongated, curved tip.

FIG. 6 shows the proximal-most portion 610 of a micro-surgery hand-piece 600 having a tip 601 with a curved extension 602. Proximal portion 610 is essentially the same as the proximal portion 210 of hand-piece 200 shown in FIG. 2, except that tip 601 has curved extension 602 and is welded into cylinder body 2, similar to the design of proximal portion 1110 of hand-piece 1100 shown in FIG. 11. As with hand-piece 1100, the curvature of tip 1 in hand-piece 600 as measured by angle a may be fixed to any angle, as required. The direction of the curvature can be directed straight ahead, to the left or right, or with an angle to the right or left. The length of extensions 602 and 1102 relative their respective diameters may be tailored to be ideal for different types of operations.

Figure 3:
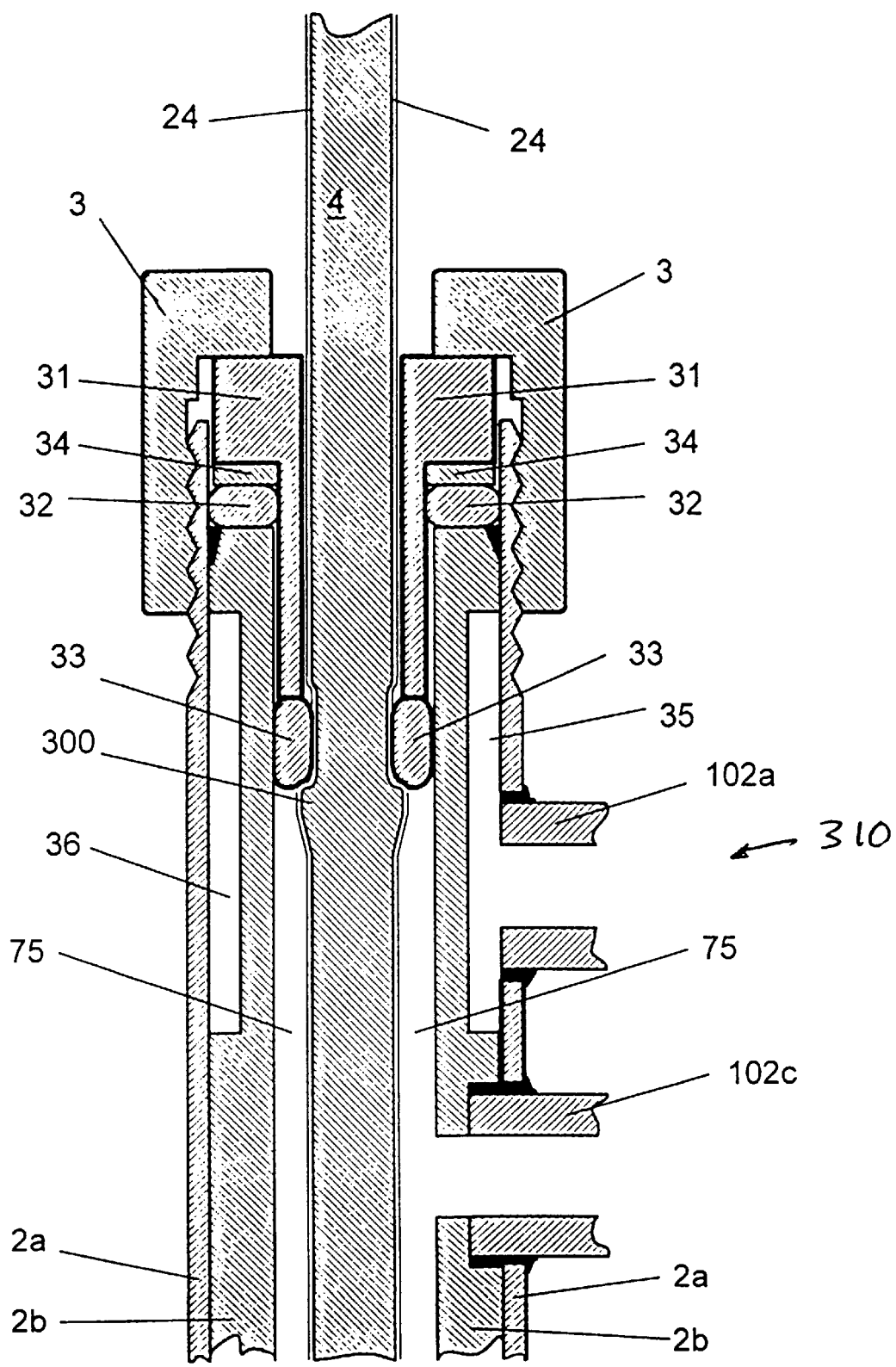
FIG. 3 shows a longitudinal section view of the distal portion of the hand-piece body of FIG. 2A.

FIG. 3 shows distal end 310 of hand-piece 200. Negative pole rod 4 is isolated from body 2 by insulative coating 24, insulator 31, and O-ring 33. Cover piece 3 applies compressive force through the insulator 31 on top of O-ring 33, which transmits the force to negative pole rod 4 at flange 300, to keep the pole rod fixed on top of the insulator 21 as shown in FIG. 2. Gas and cooling water operations are essentially the same as described with respect to FIGS. 8A–8D.

Figure 9:
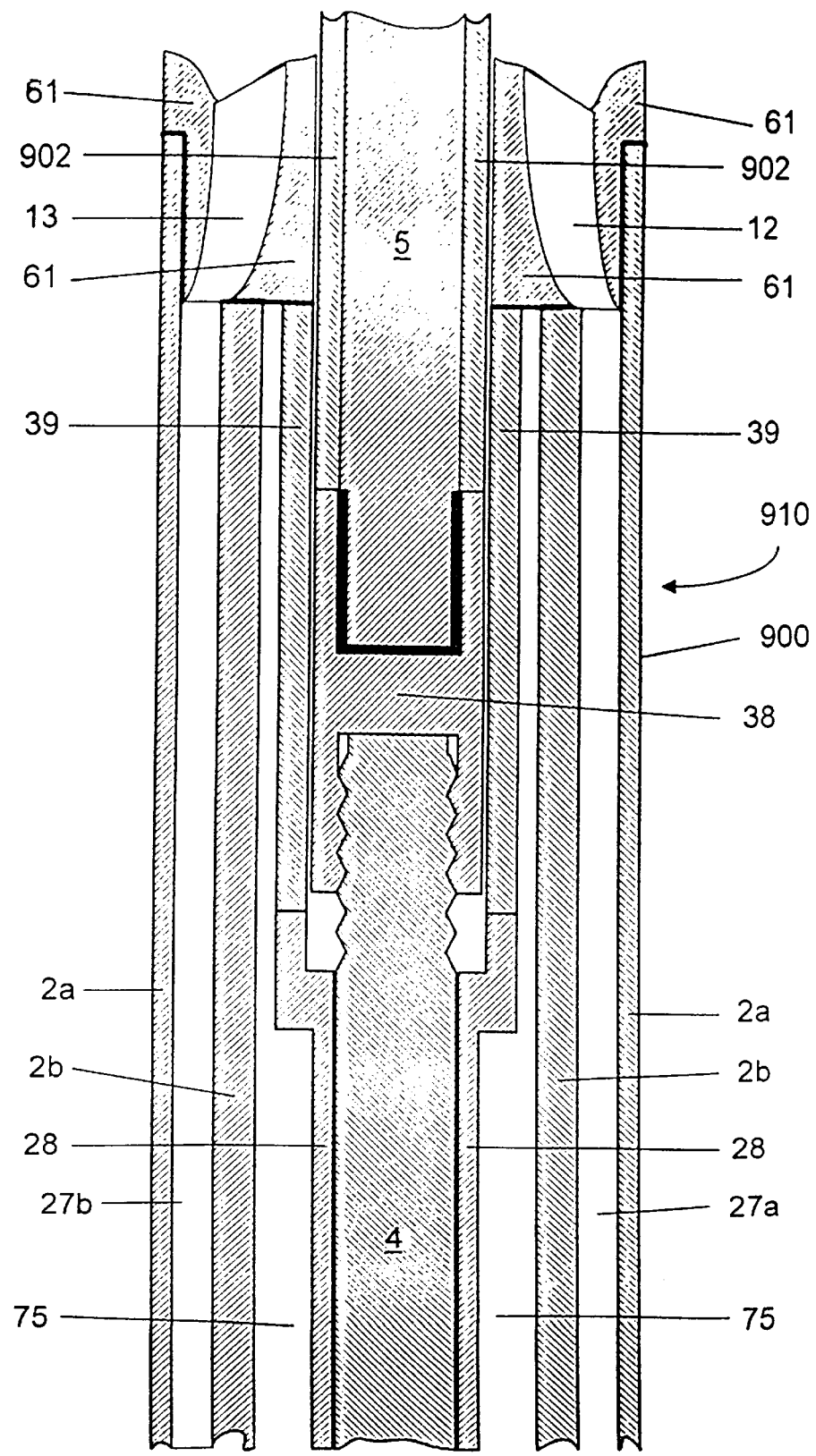
FIG. 9 shows a longitudinal section view of the proximal portion of an exemplary hand-piece body.
Figures 10A, 10B:
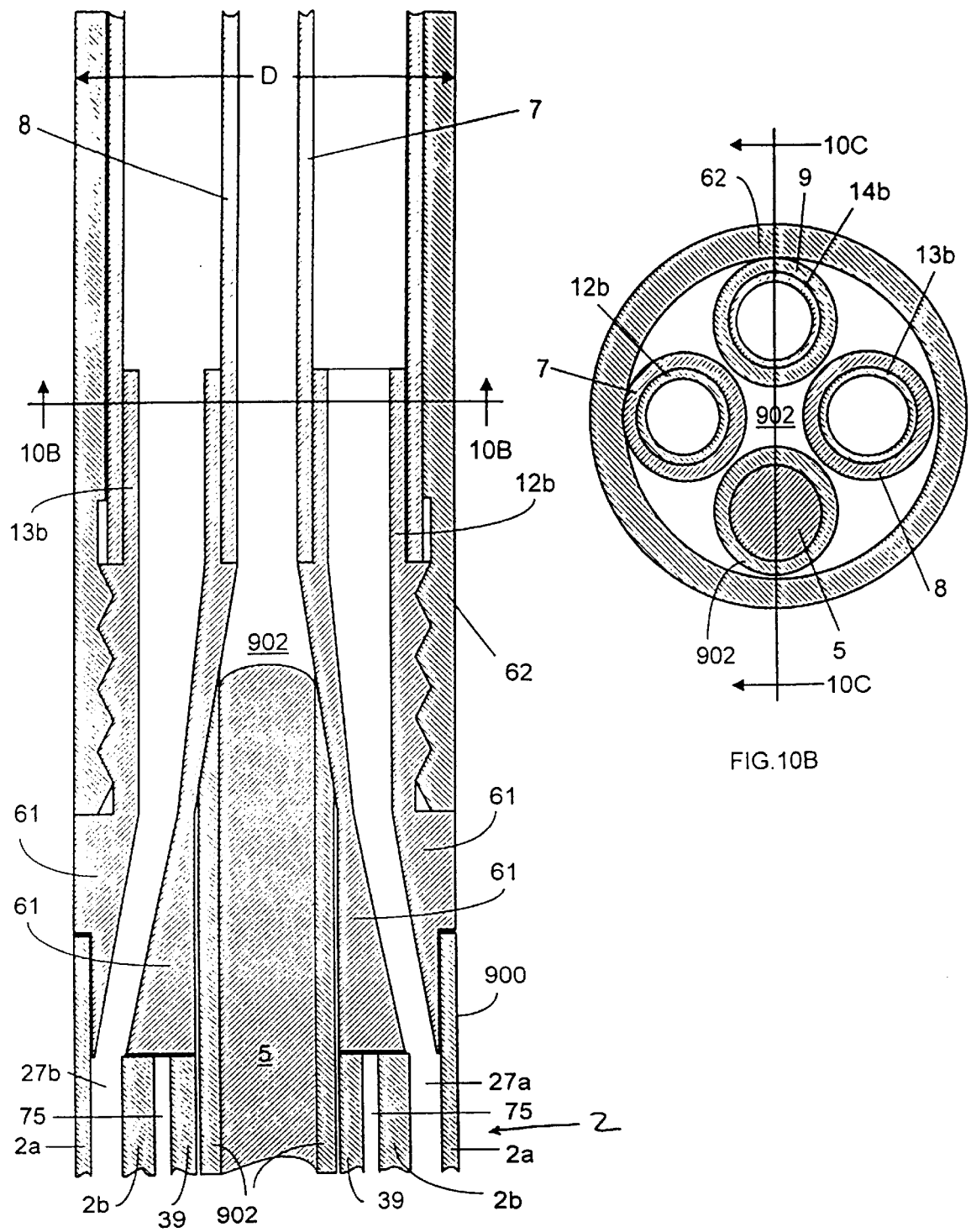
FIG. 10A shows a longitudinal section view of a distal portion of another exemplary hand-piece body.
FIG. 10B shows a cross-sectional view across line 10B—10B shown in FIG. 10A.

Referring now to FIGS. 9 and 10A–C, hand-piece 900, such as is preferably used for endoscopic or laparoscopic surgery, is constructed from three different units. The proximal portion 910 (shown in FIG. 9) is essentially the same as the proximal portions 710 or 1110 of general surgery hand-pieces 700 or 1100, as shown in FIGS. 7 and 11, respectively. Such a proximal portion is then attached, preferably welded, to connection piece 61 as shown in FIGS. 9 and 10A. Connection piece 61 is an intermediate unit that is connected to distal elongated unit 62, as shown in FIG. 10A. Connection piece 61 is structured to adapt the annular cylindrical structures of proximal portions 710 and 1110 of hand-pieces 700 and 1100 to the discrete tubular structures of elongated unit 62. Distal elongated unit 62 is preferably rigid, but may also be partially flexible if required.

As shown in FIG. 9, negative pole rod 4 screws into coupling 38, which is already connected, preferably welded, to negative pole cable 5. Insulator 39, preferably alumina ceramic, electrically insulates this connection. Cable 5 is isolated by insulation 902, typically silicon, and begins in the center of connection piece 61, but because of its elasticity, is typically directed to one side at the connection point with elongated unit 62, as shown in FIGS. 10B and 10C.

Elongated unit 62, which typically is conductive, is biased to the positive or ground voltage, which is then transmitted to connection piece 61 and ultimately to body 2. The exterior surface of the elongated unit 62 is typically coated with an insulating material (not shown), such as plastic.

Figure 10C:
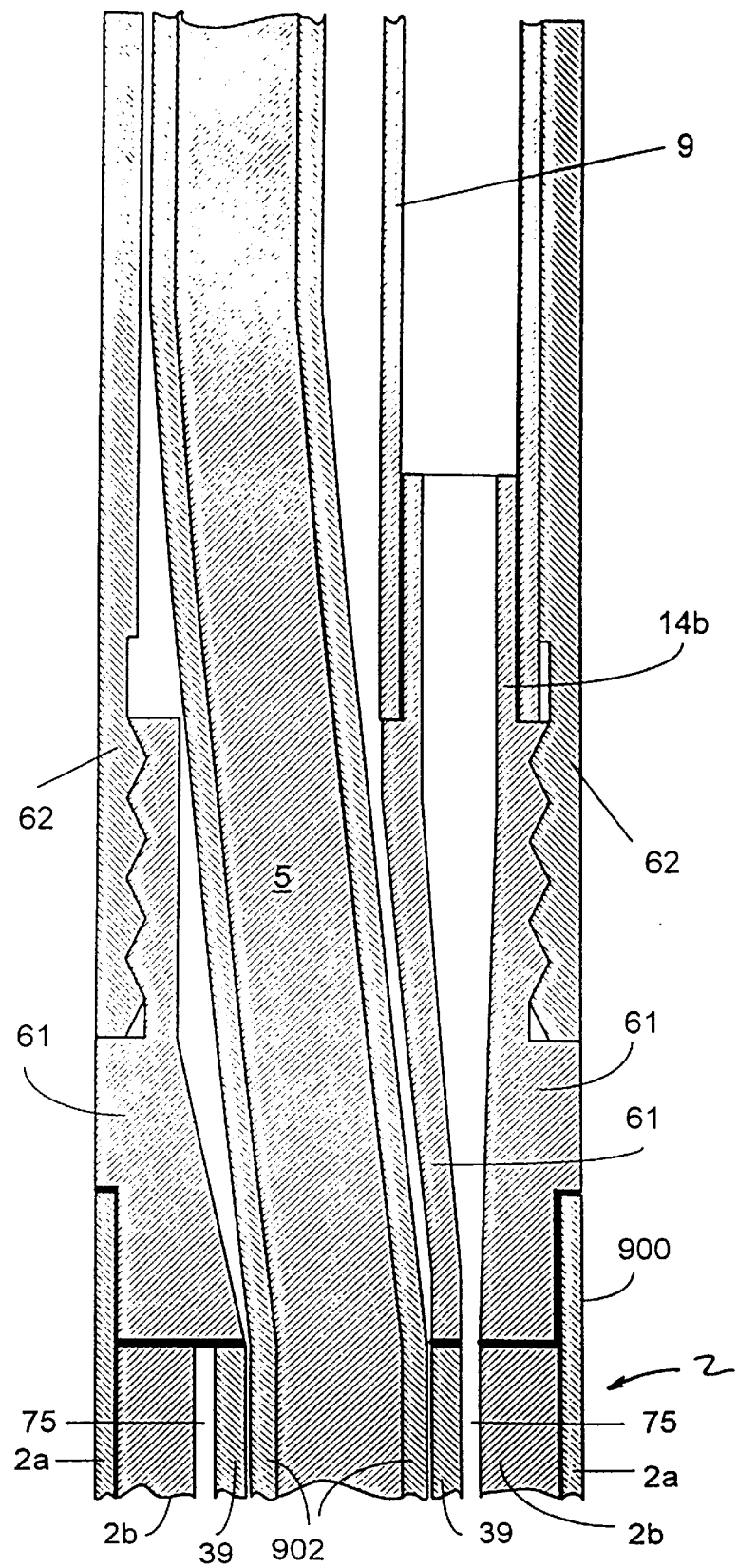
FIG. 10C shows a cross-sectional view across line 10C—10C shown in FIG. 10B.

In operation, inert gas is brought to connection piece 61 via an elastic tube 9 that is connected, such as by glue, to rigid, tubular connector 14*b* of connection piece 61, as shown in FIG. 10C. Tube 9 typically comprises a polytetrafluoroethylene (PTFE) resin such as Teflon®, manufactured by DuPont of Wilmington, Delaware, or silicon. Connector 14*b* typically comprises metal. The gas then flows into the annular channel 75 between insulator 39 and body inner cylinder 2*b*.

Cooling water is brought to connection piece 61 via elastic tube 7 (typically Teflon® or silicon) that is connected (typically glued) to rigid (typically metal) tubular structure 12*b* of the connection piece, as shown in FIG. 10A. The cooling water is conveyed into longitudinal inlet cooling channel 27*a* and, after reaching the circular channel 26 as described with respect to FIG. 7, returns through longitudinal outlet cooling channel 27*b*. Outlet cooling channel 27*b* is connected to rigid tubular structure 13*b*, to which elastic tube 8 is connected in a similar fashion as tube 7 is connected to structure 12*b*.

The outer diameter D of elongated unit 62 is typically about 10 to about 14 mm using the components mentioned above, but can be smaller to mate with a corresponding proximal portion such as portions 210 or 610 as shown in FIGS. 2 and 6. For the insulator-coated pole rod 4 shown in FIGS. 2 and 6, a portion of the pole rod is uninsulated and threaded to enable a conductive connection with connector 38.

For general surgery, the tissues to be cut, ablated, or coagulated have relatively large dimensions, so the total energy needed is relatively large. The quantum energy can range from low to high, depending on the density of the tissue. For example, lung tissue requires less quantum energy than liver tissue, which in turn requires less quantum energy than bone tissue. Because of the relatively high total energy requirement, cabinet 40 tends to be larger for general surgery embodiments than for other embodiments discussed herein, and pulsative DC power supply 41 typically emits a curve similar to that shown in FIG. 4A, with about 500 W peak power at maximum power. Impulse voltage source 42 typically comprises a high voltage (about 1000 to about 1500 V), high energy source (about 0.15 to about 0.5 watt-seconds). Hand-piece 47 typically has a diameter D (shown in FIG. 1) in the range of about 10 to about 14 mm and a length L of about 50 to about 150 mm, but dimensions smaller or larger may be used. The hand piece typically resembles those shown in FIGS. 1, 7, 8, and 11, discussed above. The channel at the tip of the hand-piece for emission of the gas stream has a diameter (d as shown in FIGS. 7 and 11) in the range of about 0.5 to about 1.2 mm. PLC 43 has power curves tailored for these hand-piece models and applications. The curved tip such as shown in FIG. 11 may be used for evaporation and coagulation of the walls of the tissues, and to cut pieces of tissues from behind the tissue while held with a pincer.

For micro-surgery, the tissues to be cut, ablated, or coagulated have relatively small dimensions, so the total energy needed is relatively small so as not to affect surrounding tissue. The quantum energy can be low or high, depending on the type of tissue to be operated upon. For example, brain tissue typically requires lower quantum energy than spinal tissue. Micro-surgery embodiments, such as for brain, spine, arthroscopic, skin surgery, and other micro surgery, typically provide low total energy and low quantum energy. Cabinet 40 tends to be smaller; pulsative DC power supply 41 typically generates voltage curves such as are shown in FIGS. 4A or 4B, with a peak power of about 200 Watts; and impulse voltage source 42 is a low voltage (about 500 to about 1000 V), low energy (about 0.04 to about 0.15 watt-seconds). The size of cabinet 40 is typically affected by the size of the power source, water system, and tubing required. A larger power source requires more cabinet space and more cooling, which requires a larger water system and larger diameter tubing to handle the water flow. Hand-piece 47 typically has a diameter D in the range of about 5 to about 8 mm, and a length L in a range of about 50 to about 120 mm, but dimensions smaller or larger may be used. Hand-piece 47 typically resembles the hand-pieces shown in FIGS. 1, 2, 3, and 6, described above. The channel at the tip of the hand-piece for emission of the gas stream has a diameter (d as shown in FIGS. 2 and 6) in the range of about 0.25 to about 1.0 mm. PLC 43 is equipped with software tailored for the hand-pieces and operative applications. A curved tip, such as shown in FIG. 6, is used to evaporate and coagulate the walls of the tissues, and to cut pieces of tissues from behind the tissue in a narrow channel while the tissue is held with a pincer, as for example, is often done during brain surgery.

For endoscopic and laparoscopic surgery, the tissues to be cut, ablated, or coagulated have relatively medium size dimensions. Thus, a relatively medium total energy is required so as not to affect surrounding tissue. The quantum energy can vary from low to high, depending upon the tissue on which the operation is performed. For example, lung tissue requires less energy than liver tissue, which requires less energy than stomach tissue. Endoscopic and laparoscopic embodiments typically provide medium total energy and medium quantum energy. Cabinet 40 tends to be relatively larger than for micro surgery models; pulsative DC power supply 41 uses curves as shown in FIG. 4A or 4B, with a peak power of about 300 W; and impulse voltage source 42 is a medium voltage (about 800 to about 1200 V) and medium energy (about 0.1 to about 0.25 watt-seconds) model. Hand-piece 47 has a typical diameter D (shown in FIG. 9) in a range of about 8 to about 12 mm, but dimensions smaller or larger may be used. Hand-piece 47 may have any length necessary, and generally conforms to hand-pieces shown in FIGS. 9 and 10A–C, with proximal portions that resemble those shown in FIG. 2, 6, 7 or 11 and described below. The channel at the tip of the hand-piece for emission of the gas stream has a diameter (d) in the range of about 0.5 to about 1.0 mm. PLC 43 has software programs tailored for the hand-pieces and operative applications. Curved tips on endoscopic or laparoscopic models may be used to evaporate and coagulate the walls of the tissues. For a laparoscopic model, the curved tips may also be used to incise pieces of tissues from behind while the tissue is held with a pincer.

For each of the apparatus types, it may be optimal to pair a particular channel diameter (d) in the tip with a desired total energy setting, as the total energy is a function of gas flow, and gas flow may be greatly affected by the tip diameter. Thus, a small diameter embodiment may provide a more precise stream than a larger diameter embodiment. For hand-pieces without a curved tip, the tip may be removable such as by a screwed connection, so tips having various channel diameters may be provided for use with a single hand-piece. For hand-pieces with curved tips, the tips are preferably welded in place to precisely set the direction of the curvature in relation to the hand-grip. For applications where the precision of the direction of curvature is less critical, a selection of hand-pieces, each with a different channel diameter and/or tip curvature, may be provided to provide different gas stream profiles.

In micro-surgery, for example, it is important to choose a hand-piece having a tip with a hole diameter large enough to provide sufficient energy to perform the desired surgical process (cutting, cauterizing, evaporating, or sterilizing) on the tissue being operated upon, but small enough to provide the necessary precision not to affect nearby tissues. Furthermore, the total energy level may be chosen at a level small enough not to create an unacceptable "blast effect" for the tissue being operated upon. The blast effect of a gas is defined by its momentum (mass times velocity=m×v) which is absorbed by the matter that the gas hits. As the mass or velocity of the gas increases, the blast effect increases. In the system of the present invention, the velocity is a function of the quantum energy and the mass is a function of the total energy. The tip diameter of the hand-piece also impacts upon the mass, as the number of atoms leaving the channel is proportional to the square of the tip diameter. Minimizing or eliminating such a blast effect may be particularly important when operating, for example, on brain tissue, which is sensitive to such effects. The quantum energy is selected depending on the type of tissue to be operated upon. Thus, hard tissues such as the spine may require higher quantum energy than for a soft tissue such as the brain.

During operation of the apparatus using, inert gas atoms, typically argon, are brought from gas container 48 through gas control system 49 (as shown in FIG. 5), through elastic tube 9, connectors 14a or 14b, and tube 102c or connection piece 61 (as shown in FIG. 1 or 10C, respectively), into channel 75 between negative pole rod 4 and body inner cylinder 2b, and through gas channels 25 in the end of negative pole rod 4 to plasma cell 23. Voltage from impulse voltage source 42 (to trigger the plasma) and pulsative DC power supply 41 (to sustain the plasma) are carried to the hand-piece via a common pair of cables 5 (negative) and 6 (positive and grounded). The negative voltage is conducted via cable 5 to negative pole rod 4 through connector 11 (shown in FIG. 1) or 38 (shown in FIG. 10), and transmitted to tungsten electrode 22, which is disposed in the end of negative pole rod 4. Positive voltage cable 6 is connected to body 2 through pipe 102a or pipe 102b (as shown in FIG. 1) or through connection piece 61 and elongated unit 62 (as shown in FIG. 10A), thus transmitting the positive and grounded voltage to the respective hand-piece tip through body 2.

Insulator 21 around the plasma cell 23 electrically isolates negative pole rod 4 from body 2. Insulator 21 also transmits some of the thermal energy of the atoms to body 2. The most proximal part of plasma cell 23 comprises gas channel 220, 620, 720, or 1120 as shown in FIG. 2, 6, 7, or 11, respectively, built into respective tips 201, 601, 701, or 1101. Water circulation channel 26 is positioned very close to plasma cell 23 to cool the proximal portion of body 2 as well as electrode 22, insulator 21, and the majority of the tip. Because of the effective cooling, body 2, except the most proximal part of the tip, does not convey any heat to the tissues. The cooling water is pumped by cooling water pump 51 from cooling water tank 50 (as shown in FIG. 5), through tube 7, connector 12a, tube 102a, and cooling water input channel 35 (as shown in FIGS. 3 and 8), or through tube 7 to connector 12b at connection piece 61 (as shown in FIG. 10A), and into longitudinal cooling water inlet channel 27a. Channel 27a brings the cooling water to cylindrical channel 26 and back through longitudinal cooling water outlet channel 27b. The cooling water then exits through cooling water output channel 36, tube 102b and connector 12a (as shown in FIGS. 3 and 8) or through connection piece 61 and connector 12b (as shown in FIG. 10A), and finally through the cooling tube 8 back to cooling water tank 50. The cooling system typically uses sterilized water.

To start the apparatus, gas container 48 (shown in FIG. 5) is connected, its valve is opened, and its mechanical regulator is adjusted to provide an input pressure of approximately 8 Atmospheres. The apparatus is plugged in, and a suitable sterilized hand-piece 47 is connected to cabinet cable and tube system 53 via quick connection piece 54. Electrical power is turned on using power switch 1300 on control panel 44 (as shown in FIG. 13). The cooling system immediately starts to function. If the gas container pressure is too low or too high, this is indicated on control panel 44 via indicators 1301 and 1302, respectively. If the main power voltage is not correct, or the water is not circulating, this is also indicated on the panel 44 by indicators 1303 and 1305, respectively, and in either case ERROR indicator 1306 is illuminated. When the ERROR indicator 1306 is lit, the apparatus can not be started.

By pressing check switch 1307, the operator can determine if all the check points are OK. If so, indicator 1308 is lit to prompt the operator to choose one of the quantum energy levels by pressing one of switches 1350–1354. The light corresponding to the switch chosen and "ready" light 1343 are then illuminated. Pushing "start" switch 1341 initiates plasma generation. First the gas valve (not shown) in gas control system 49 is opened by PLC 43, and after a first defined time, impulse voltage system 42 is activated to trigger the plasma for a second defined period of time. During this period of time, this impulse may be automatically repeated several times if the plasma is not initiated right away. The first and second defined times may be input parameters for the PLC 43. Impulse voltage system 42 typically delivers an impulse voltage of approximately 1000 volts. The voltage and power values may vary for different types of equipment, however. When the negative voltage is applied to electrode 22, a corona discharge (a local ionization of the gas, due to the electrons issued from the sharp-point of the electrode with high electrical field), is created on the tip of the electrode. The electrons break loose additional electrons from the inert gas atoms due to the very high value of the voltage applied. With new each ionization, the number of electrons grows moving toward positive pole of the plasma-cell 23, which is the outer borderline of plasma-cell volume as defined by the tip 1.

As the ionization grows, the volume within plasma-cell 23 becomes more electrically conductive (because more electrons are present). Consequently, electrons can be transferred from the tip of the electrode 22 at lower voltages. At this point, pulsative DC power supply 41 takes over transfer of the electrons from negative electrode 22. The kinetic energy of the particles is initially low, so at least the ionization voltage of the inert gas (15.75 V for argon) is initially applied between the electrodes to ionize the inert gas atoms. Once the atoms are energized by the ions and electrons, the voltage that is needed to ionize them is decreased to keep the number of ions and the energy level constant in the plasma cell. This is due to what is commonly called the "negative impedance effect" of the plasma. Practically, it means that if the voltage on the electrodes is kept constant, ionization and energy at the area is continuously going to increase. For this reason, the electrical power supply of the present invention may be referred to as a "current source" rather than a "voltage source," because it controls the number of the electrons provided to the system.

Especially when the apparatus starts with cool gas atoms, a low quantum energy, and a low total energy, the current calculated by the PLC System 43 may be too low to be able to initiate a continuous plasma. Thus, for each quantum energy setting, a temporary current may be defined in the PLC that is applied together with the calculated current. This additional current, which has the same sharkfin-shaped curve as the main current, is decreased to zero within a defined time period of typically a few seconds. This defined time period can be set in the PLC as an input parameter. Using the combination of a temporary and a calculated pulsating current allows for a continuous plasma to be obtained even if the quantum energy and the total energy starting parameters are very low.

Because of the voltage applied between the electrodes, an electrical field is present throughout the volume of plasma cell 23. Electrons move towards the positive pole, getting energy from this field, and ionized atoms move towards the positive pole, also getting energy from this field. Thus, electrical energy is transferred into kinetic energy. While moving in the electrical field, both electrons and ions hit inert gas atoms and share their kinetic energies with those atoms. When the energy of some of the individual electrons reach the ionization energy of the atoms, they break loose new electrons from the atoms. When the electrons reach the positive pole, they are transferred to the positive pole of the power source. When ionized atoms reach the negative pole, they are neutralized by the receipt of negative electrons. Gas atoms passing through plasma-cell 23 are continuously hitting each other and homogenizing their energies.

In this way the majority of the atoms obtain energies close to the average energy of the atoms. There are some atoms, however, having energies greater or smaller than the average energy. The overall distribution of atom energies conforms to a bell-curve distribution. Because a minimum possible ionization voltage is desired, argon gas is preferred for use in the apparatus of the present invention, because argon is the inert gas with the lowest first electron ionization energy among the most practically available inert gasses. The ionization energy for argon is 15.75 V, as compared with 21.56 V for neon and 24.57 V for Helium. Thus, the bell-curve that defines the temperature distribution of argon atoms is narrower than for neon and helium. Basically, the gas pressure and partly the electrical field of the ions (minus the voltage applied) push the atoms through the channel. The inert gas ionization energy is therefore a controlling factor in how much voltage needs to be applied to the plasma cell, and thus the application voltage differs for each type of gas.

Once plasma starts building in a chain reaction, the number of electrons is kept under control using the pulsative DC power supply 41, and a steady state is obtained in which the gas flow, total energy, and quantum average energy of the atoms have stable values. Positive ions in plasma cell 23 are attracted by the negative pole and pushed inwards towards the negative electrode by the positive pole around it. The positive electrode collects electrons coming out of the negative pole. Only the non-ionized atoms are pushed towards the tip of the hand-piece by the gas pressure. As the non-ionized atoms move toward the discharge end of the tip, their individual energies get more equalized through collisions, and they lose energy to the wall of the channel (such as channel 220 in FIG. 2). Particles with high kinetic energies may radiate photons in accordance with their temperatures. These energy releases and losses mean that the atoms actually emitted from the tip have lower and more homogenized energies than in plasma cell 23. It is desired to control the quantum energy level of these emitted atoms. Because of losses to the channel wall throughout the length of the channel, the diameter and length of the channel affect the final average temperature.

At a certain distance from the most proximal point of tip 201, the atoms start losing their kinetic energy through collisions with air molecules and the like. Depending on the amount of the total energy the atoms have when exiting tip 201, and depending on the diameter d of the channel, this distance is typically in a range of about 2 to about 10 millimetres.

Particles having high kinetic energies radiate photons. The frequency (or the energy) of the photons depends on the kinetic energy (or quantum energy, or temperature) of the particles. When the particles exit the nozzle with a sufficiently high kinetic energy, they become visible because these particles radiate photons in the red to violet visible light spectrum. One way to measure the quantum energy level or temperature of the atoms is by measuring the frequencies (color) of the photons radiating from the beam. In very high energy applications, the photons are ultraviolet. The ultraviolet radiation generates a limited amount of ozone gas in the air. The amounts of photon radiation and ozone gas are minimal enough, however, that they pose no danger to the patient, the operators, or the operating room environment.

Essentially none of the ions created in plasma cell 23 are emitted through channel 220, because the positive voltage applied on the channel pushes the positively-charged ions back towards negative pole 22. Electron emissions from the channel are also essentially none, because the electrons are drawn by the positive pole of the wall of the channel 220. The term "essentially none" as used herein means none or some barely definable amount. It is estimated that the quantity of ionized inert gas atoms in the plasma cell is quite small, somewhere between $10^{-4}$ to $10^{-5}$ times the total number of atoms present in the system. Only a small fraction of this fraction may potentially escape, meaning that practically none actually escape. Thus, essentially only neutral atoms are emitted, which have no charge to transfer to the tissues. Because the positive pole of the hand-piece is typically connected to ground, it can not transfer any current to the tissue if it touches the tissue. Thus, there is no transfer of current from the hand-piece or gas stream to the tissue, the body of the patient, or the operator.

To keep the quantum energy constant, when the total energy is variable, the total number of atoms is adjusted. To increase or decrease the total energy coming out of the tip of the tool, the gas flow is adjusted by pressing on the "energy up" or "energy down" switches on control panel 44 or the foot pedal 45. The gas flow is increased or decreased continuously for as long as the switches are depressed, as a result of a voltage from PLC 43 activating a pressure or flow regulator for gas control system 49 in one direction or the other, for example using a system such as is shown in FIG. 16. The gas flow is typically measured with a flow meter directly or with a pressure device indirectly.

In conjunction with the increased gas flow, the electrical energy of the power supply is increased or decreased accordingly based upon the gas flow measurement. The electrical current needed is calculated by the PLC System 43 continuously for the selected quantum energy level (chosen by pressing on one of the five switches 1350–1354) based upon one of five different corresponding current curves kept in the memory of PLC 43. Depending on the quantum energy value setting, PLC 43 calculates the electrical current required for the given gas flow, and applies the necessary voltage to obtain this current between the electrodes. The basic logic increases the current (energy) applied between the electrodes in steps to increase the quantum energy of the atoms for the same gas flow. Stepwise decreases are similarly used to decrease the quantum energy.

The dimensions and geometry of tip 201 and channel 220 affect the quantum energy because the amount of atomic energy lost to the conductive walls of tip 201 depends on dimensions and geometry of tip 201 and channel 220. Thus, the family of curves defined in PLC 43 makes it possible to obtain the required quantum energy level for the type of operation desired for different types of hand-pieces. For example, the same quantum energy level may be obtained by selecting the medium quantum energy level for one hand-piece and the "high" energy level for another hand-piece. Because the color of the stream of atoms visible to the operator is indicative of the quantum energy, the operator may be able to select the quantum energy switch that produces the color that is known by experience to work the best for the particular operation.

The quantum energies of atoms can be adjusted for between about 2,000 K to about 35,000 K, or broader. Because the quantum energy of the inert gas stream is below the ionization energy of any atoms in the molecules of tissue or air that the stream contacts, even at 35,000 K (4.5 eV equivalent) the inert gas stream does not ionize any of these molecules, thereby avoiding the formation of potentially harmful "free radicals." A relatively small amount of ionization, however, may be caused by any emitted ultra-violet radiation.

When the hand-piece is brought very close the tissue to be operated upon, and when the energized atoms coming out of the tip of the hand-piece are applied to the tissue, these atoms hit the bio-molecules with high quantum energies. Because the kinetic energy of the atoms is larger than the bonding energies of the smaller molecules that comprise the bio-molecules, the smaller molecules are broken and they evaporate (sputter). If the total energy and the quantum energy is high, this happens very quickly. When the energy parameters are lower, it takes a longer time.

Depending on the whether the tissues are brain, lung, liver, or bone, different quantum energies are needed. To sputter (evaporate) tissues like bone, higher quantum energies are required, while for brain tissue, lower quantum energies are required. Different total energies may be required depending on the type of operation in conjunction with the type of tissue. For example, the apparatus may be adjusted to very low total energy for microsurgery so as to only affect the operative tissues thermally. For liver surgery, however, the size of the tissue involved in the operation is much larger, so the total energy needed is typically larger.

Figure 15:
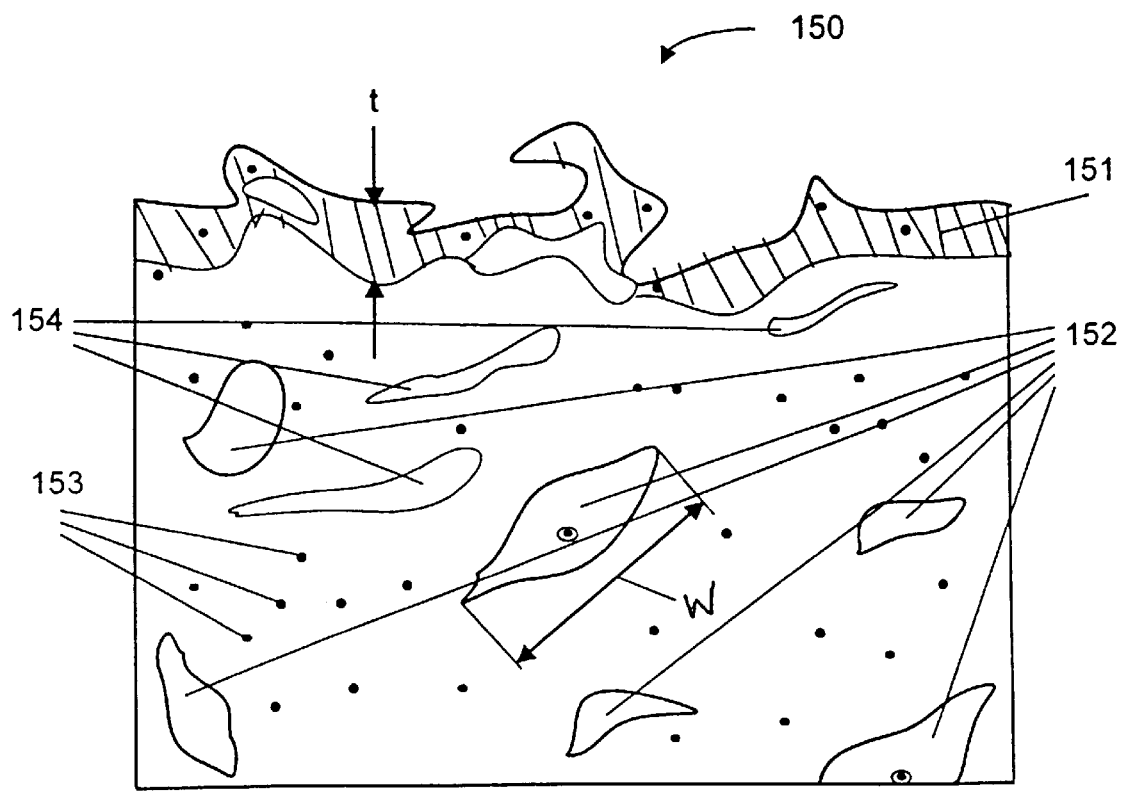
FIG. 15 is a cross-sectional diagram illustrating an exemplary portion of brain tissue after having been treated using an exemplary device of this invention.

Referring now to FIG. 15, there is shown an exemplary cross-sectional portion of tissue 150 showing nerve cells 152, neuroglial cells 153, and vascular and lymphatic channels 154, after a sputtering operation using an exemplary embodiment of the present invention has removed tissue (not shown) above cyst wall 151. During the process of evaporating the sputtered tissue, when bio-molecules are broken into smaller molecules, kinetically energized molecules and the lower energy atoms hit the molecules underneath the sputtered molecules and increase the temperature of the underlying molecules. This dehydrates a small amount of tissue 150 and destroys some neuroglial cells 153 and nerve cells 152, which then form cyst wall 151. The total thickness (t) of cyst wall 151 of dehydrated and/or destroyed tissue using a micro-surgery embodiment of this invention is typically less than about 10 micrometers ($\mu$m), which is approximately one-third to one-fourth the typical width W (about 30–40 microns) of a nerve cell 152 in the brain. The cyst wall thickness using general surgery embodiments on other types of tissue is typically on the order of about 10 to about 30 microns.

The amount of surrounding tissue damaged through the use of the present invention is an advantage over previous technologies. For bipolar equipment, the thickness of the cyst wall is about the size of the electrodes, which is millimeters (thousands of microns) thick. For lasers, the cyst wall thickness can be controlled to lower values. The tissue damaged by a laser, however, is not limited to the cyst wall, as individual cells far behind (several millimeters away) the cyst wall can be damaged due to individual photon penetration from the laser beam. This damage, because of its molecular dimension, is not readily measured, but has been hypothesized to potentially have future ramifications, such as leading to cancer. For this reason, lasers are not approved for many surgical procedures. The atoms emitted by the apparatus of this invention, being unable to penetrate through the molecules of tissue like photons, can only apply their energy to the first molecule they hit.

Because of the relatively small thickness of the cyst wall, there are typically only a very small amount of dead cells left in the operation area when the operation is completed. This means there are fewer post-operative problems for the patient. The dead tissue left behind helps to guarantee that there are no bleeding vessels or other open channels, such as bile ducts, thin bronchia, lymphatic vessels, and the like, losing fluid, such as liquid or gas (air), therefrom, because all such vessels are constricted and tapped. Thus, evaporation of tumor tissue can be accomplished without transfer of cells to other tissues, since there are no open channels remaining behind.

Deep penetration into the tissue is obtained by holding the plasma beam longer, and moving it inwards toward the body. The tissue evaporated during this procedure will have a diameter somewhat larger than the beam diameter. By using a very short beam time period, the evaporation can be limited to the surface of a tissue. Thus, for example, part of epidermis can be destroyed without applying anesthetic agents, because the dermis, where pain is detected, is not affected.

Resection of a tissue is accomplished by moving the hand-piece on a line. First a shallow channel is created. Moving the hand-piece on the same line makes the channel deeper and deeper so that finally the tissue is resected. For very thick tissues, to bring the body of the hand-piece deeper in, the operator can hold the part of the tissue to be resected so that the already-created channel widens to allow further penetration of the hand-piece into the tissue. Because a thin cyst is also created during such a procedure, the cyst helps to provide a bloodless operation. As a result, tissues, in particular bleeding-prone tissues such as spleen, liver, lung, pancreas, kidney, brain and the like may be resected without stitching. Cyst creation also minimizes the risk of tumor cells transferring during the resection.

Large body lumen, such as veins, arteries or other vessels or ducts, can be cut by first constricting them with low energy, and then cutting them with high energy. For example, the lumen to be cut may be first pulled away from surrounding tissue so that the procedure does not affect the surrounding tissue. Then the tip of the hand piece is adjusted for medium energy and applied to the surface of the lumen by moving the gas stream longitudinally back and forth along the lumen from about a centimeter away or less. This constricts the lumen smoothly without perforating it. Then, the apparatus is adjusted for medium or high energy and the gas stream is applied crosswise in the middle of the constricted lumen from a very close distance to incise it.

By adjusting the apparatus to low quantum energy levels, surface bleeding of a tissue can be coagulated. For example, the apparatus may be adjusted to a low energy level and the hand-piece spaced a close distance from the area to be cauterized. The tip of the hand-piece may be moved along a wide surface of the tissue to create a cyst wall to close any bleeding channels. Another method of cauterizing tissue is to adjust the apparatus to a higher energy level, but with a relatively greater distance, such as a few millimeters to a few centimeters depending on energy level, between the hand-piece and the area to be cauterized, to create the cyst wall. A damaged and bleeding organ can also be coagulated this way. When adjusted at the high-quantum-energy setting, the apparatus can provide urgent point-wise coagulation over a larger area to be cauterized. The above methods can be used with a very low energy setting from a distance of a centimeter or a higher energy setting from a distance of a few centimeters, to sterilize infected tissue by creating a cyst wall.

Evaporation of a large tissue region requires a correspondingly large amount of energy and high-energy transfer. Therefore, to remove a large region of unwanted tissue, the tissue is preferably cut into pieces and removed, thus minimizing the amount of energy transfer. This method is particularly important for brain surgery. Relatively small amounts of tissue can be removed by evaporation alone even for brain surgery, however, as the amount of energy transferred by the present invention is less than the amount of energy transferred by the metal of bipolar cautery equipment currently used for brain surgery. One can also use water cooling of the tissues in conjunction with the present invention when it is needed, as is done when using standard cautery equipment.

Because bone tissue is highly thermally conductive, cutting bones with the present invention is best performed underwater, as is typically done with circular saws. Thus, the apparatus of this invention may be operated with at least a portion of the hand-piece tip submerged underwater. As used herein, "underwater" may mean under water or under any suitable fluid used for the surgical procedure, such as a saline solution.

Different operations such as brain surgery or surgery of the liver, require different total energy and different quantum energy. To increase the quantum energy while keeping the total energy constant, the electrical energy must be kept constant while the gas flow is decreased. To decrease the quantum energy while keeping the total energy constant, the electrical energy must be kept constant while the gas flow is increased. Changing the quantum energy is performed from the control panel by pushing on one of the five power switches 1350–1354. Control of the total energy is accomplished using foot pedal 45 or from control panel 44, by pushing the "energy up" switch 1322 or "energy down" switch 1320.

The present invention offers many advantages of methods and apparatus known in the art. The present invention allows the vaporization of large amounts of tissue with minimal damage to neighboring tissues, with minimal or no blood loss. The apparatus of this invention may be used on any body tissue, including but not limited to brain, lung, liver, kidney, stomach, and the like. In general, higher quantum energies are required for hard tissues such as bone or cartilage, than for softer tissues such as skin or organs. Resection may be performed as a thin line evaporation. Tumor extraction may be realized as large-volume tissue evaporation. Minimized bleeding during operations using the present invention makes such operations very fast with minimal or no blood loss. Additionally, stitchless operations or operations with minimum stitching can be performed on tissues like the lung, liver, gallbladder, spleen, and the like. This also shortens the total time of the operation. The typical closing of venules, arterioles, lymphatic channels, and micro-circulatory vessels during operation with the apparatus of this invention means minimal or no risk of metastasis for malignant tumors. Post-operative complications and patient recovery time is significantly reduced since the dead tissue left behind is only about one cell thick for the brain and typically no more than about three cell layers for the other soft tissues.

The potential for bloodless tissue evaporation with the present invention makes new types of operations possible that were not imaginable previously. For example, one can destroy a tumor by applying the beam generated by this invention directly on the tumor without cutting the surrounding tissues. The invention permits vaporization of a "thin layer" of a tissue, limiting the damage to the organ on which it is applied. Thus, the present invention may be used to remove dead tissue layers on organs, such as in the case of severe burns, or to remove large surface infections of the bones, for example.

One can use the present invention as a coagulator by using a coagulation tip such as shown in FIGS. 2, 6, 7, and 11 using a relatively small diameter (d) and/or by adjusting the energy per atom, by merely pressing a switch. The apparatus can be used as a wide surface coagulator, or a coagulator with pinpoint accuracy. One can choose to coagulate a millimeter-diameter vein or artery, or to cut it, merely by adjusting the energy level of the apparatus. By choosing the correct tips for coagulation, the present invention may be used for very large surface sterilization of the tissues. This can also be realized by merely selecting the low energy level switch at any stage in the operation. An experienced operator can cut, evaporate, or coagulate a tissue with the same hand-piece and tip, by merely adjusting the total energy level (by foot or finger) and the level of energy per atom, (by only pressing a switch).

The present invention does not transfer electrical currents to the tissues or body of the patient, and the ability to make low energy adjustments minimizes the risk of perforation of thin walled areas like veins, arteries, the colon, and the like. The apparatus emits minimal smoke and steam, and the inert gas has limited impact on the operating procedure. The apparatus further creates minimal or no interference with other typical operating room equipment and adds minimal or no unusual safety requirements to the operating room environment.

It should be noted that although the term "hand-piece" is used throughout to refer to the means for directing the energized inert gas atoms at the target for the operation, the hand-piece may not necessarily be handled by a human hand, but rather manipulated remotely by robotic controls or by any other means known in the art.

Although illustrated and described above with reference to certain specific embodiments, the present invention is nevertheless not intended to be limited to the details shown. Rather, various modifications may be made in the details within the scope and range of equivalents of the claims and without departing from the spirit of the invention. In particular, the detailed parameters provided herein related to the cabinet, control panel, impulse and pulsative power supply voltages and wattages, and various hand-piece and tip geometries and dimensions merely relate to exemplary embodiments, and by no means are intended to limit the invention to those embodiments, or the embodiments to those parameters.

What is claimed:

1. A surgical apparatus adapted to emit a plurality of high-energy inert gas atoms in a stream, the apparatus comprising:

an inert gas source;

a plasma cell in communication with said inert gas source for imparting energy to said inert gas atoms, to create energized inert gas atoms, said plasma cell defined in part by a positive electrode and a negative electrode;

at least one power supply electrically connected to said negative and positive electrodes, said at least one power supply adapted to provide (a) initially an ionization voltage between said negative and positive electrodes to initiate a plasma from said inert gas in said plasma cell, and (b) subsequently a pulsed voltage curve that sustains the plasma at a predetermined energy level; and means for directing the energized inert gas atoms at a target.

2. The apparatus of claim 1 wherein the pulsed voltage curve comprises a repeated pattern of a peak voltage for a first amount of time ($t_p$) followed by a minimum voltage for a second amount of time ($t_z$).

3. The apparatus of claim 2 wherein the pulsed voltage curve comprises a minimum voltage greater than zero.

4. The apparatus of claim 2 wherein the pulsed voltage curve comprises a minimum voltage equal to zero.

5. The apparatus of claim 2 further comprising an inductance coil through which the pulsed voltage curve is applied to create a sharkfin-shaped current curve and sharkfin-shaped voltage curve to be applied at the plasma cell.

6. The apparatus of claim 1 further comprising a control system connected to said inert gas supply and to said power supply, said control system having at least one user interface and a plurality of energy settings, said control system adapted to vary the voltage curve and the inert gas flow to provide a user-selected quantum energy and total energy level in said plasma.

7. The apparatus of claim 6 wherein the control system comprises a programmable controller, a quantum energy control user interface connected to said programmable controller, and a total energy control user interface connected to said programmable controller.

8. The apparatus of claim 7 wherein the quantum energy control user interface comprises a control panel with a plurality of switches, each switch corresponding to a desired quantum energy level.

9. The apparatus of claim 7 wherein the total energy control user interface comprises a start switch, a stop switch, a first switch for increasing power and a second switch for decreasing power.

10. The apparatus of claim 9 wherein the start switch, the stop switch, the first switch and the second switch are located on one of: the control panel, a foot pedal, or both.

11. The apparatus of claim 1, wherein the means for directing the energized gas atoms at the target comprises a hand-piece having a tubular body comprising therein said plasma cell and a tip extending from said body, said tip comprising a channel in communication with said plasma cell for emission of said high-energy inert gas atoms from said tip.

12. The apparatus of claim 11 wherein a portion of said tip is disposed within said body and further comprises said positive electrode.

13. The apparatus of claim 12 wherein the negative electrode is axially disposed within said plasma cell and said positive electrode radially surrounds said negative electrode and is spaced apart and electrically insulated therefrom.

14. The apparatus of claim 12 wherein the positive electrode is biased to ground.

15. The apparatus of claim 11 further comprising a cooling system for said hand-piece.

16. The apparatus of claim 15 wherein the cooling system comprises sterilized water.

17. The apparatus of claim 16 wherein said cooling system further comprises a water circulation system within said hand-piece.

18. The apparatus of claim 11 further comprising a hand-piece cable and tube system attached to the hand-piece and a cabinet cable and tube system attached to the inert gas source and power supply, the hand-piece and hand-piece cable and tube system attachable and detachable from the cabinet cable and tube system.

19. The apparatus of claim 11 wherein said tip is detachable from the hand-piece.

20. The apparatus of claim 18 wherein said hand-piece and a hand-piece cable and tube system comprise materials of construction adapted to be chemically or thermally sterilized.

21. The apparatus of claim 11 wherein the tip comprises an elongated, curved extension.

22. The apparatus of claim 11 wherein said hand-piece further comprises a grip.

23. The apparatus of claim 22 further comprising one or more tubular connections and an electrical connection to said hand-piece, wherein said tubular connections and said electrical connection are connected to said hand-piece at a connection region on one side of a distal portion of said hand-piece that is covered by a cover, said cover at said connection region comprising said grip.

24. The apparatus of claim 11 further comprising one or more tubular connections and an electrical connection to said hand-piece, wherein the hand-piece is adapted for endoscopic or laparoscopic surgery and further comprises a proximal portion, an intermediate connection piece mounted to a distal end of said proximal portion, and a distal elongated unit housing a portion of said tubular connector and a portion of said electrical connector, the distal elongated unit connected to a distal end of said intermediate connection piece, in which said proximal portion, said intermediate connection piece, and a proximal end of said distal elongated unit collectively comprise a continuous cylindrical periphery when connected together.

25. The apparatus of claim 24 wherein the hand-piece has a diameter (D) of less than or equal to about 10 mm and a tip channel diameter (d) in a range of about 0.5 to about 1.0 mm.

26. The apparatus of claim 11 wherein the hand-piece is adapted for general surgery has a diameter (D) in the range of about 10 to about 14 mm, a length (L) of about 50 to about 150 mm, and a tip channel diameter (d) of about 0.5 to about 1.2 mm.

27. The apparatus of claim 11 wherein the hand-piece is adapted for micro surgery has a diameter (D) in the range of about 5 to about 8 mm, a length (L) of about 50 to about 120 mm, and a tip channel diameter (d) of about 0.25 to about 1.0 mm.

28. The apparatus of claim 27 wherein the hand-piece further comprises a negative pole rod having an outer periphery and axially extending through the hand-piece to the negative electrode, said pole rod comprising insulation covering said periphery.

29. The apparatus of claim 1 wherein the inert gas comprises argon.

30. The apparatus of claim 1 wherein said high-energy atoms emitted by said apparatus have an average energy that is larger than a molecular binding energy of one or more sub-molecules that comprise the tissue on which the process is performed.

31. A method for performing a surgical procedure on living tissue using a surgical apparatus adapted to emit a plurality of high quantum energy inert gas atoms in a stream, the apparatus comprising a hand-piece having therein a plasma cell defined in part by a positive electrode and a negative electrode; a hand-piece tip comprising a channel in communication with said plasma cell for emission of said inert gas atoms from said tip in said stream; an inert gas supply connected to said hand-piece; and at least one power supply electrically connected between the positive electrode and the negative electrode; the method comprising:

(a) providing inert gas flow into said plasma cell;

(b) initially applying from said power supply an ionization voltage between said negative and positive electrodes, thereby initiating a plasma from said inert gas in said plasma cell;

(c) then applying from said power supply a pulsed voltage curve, thereby sustaining the plasma at a predetermined quantum energy level, said plasma comprising said plurality of high quantum energy inert gas atoms, a plurality of ions, and a plurality of free electrons;

(d) emitting said high quantum energy inert gas atoms from said channel in said tip; and (e) using said high quantum energy inert gas atoms to perform a surgical process on said portion of said living tissue.

32. The method of claim 31 wherein said surgical process comprises a process selected from the group consisting of: cutting, cauterizing, ablating or evaporating, sterilizing, and a combination thereof.

33. The method of claim 31 wherein said high quantum energy atoms that are emitted have an average quantum energy that is larger than a molecular binding energy of one or more sub-molecules that comprise the tissue on which the process is performed.

34. The method of claim 31 wherein said high quantum energy atoms that are emitted have an average quantum energy that is not large enough to ionize molecules of said tissue to create free radicals.

35. The method of claim 31 further comprising emitting only said plurality of high-energy atoms, and essentially none of said plurality of ions or said plurality of electrons from said apparatus.

36. The method of claim 31 wherein step (e) comprises one of: cutting an incision in said living tissue or evaporating or ablating a portion of said living tissue, and further comprises simultaneously creating a cyst wall of cauterized tissue surrounding said incision or said evaporated portion.

37. The method of claim 36 wherein said incision comprises a line evaporation.

38. The method of claim 36 wherein the surgical process comprises brain surgery and the cyst wall that is created has a thickness of less than about 10 micrometers.

39. The method of claim 36 wherein the tissue is a soft tissue and the cyst wall that is created has a thickness in a range of about 10 to about 30 microns.

40. The method of claims 36 wherein said cyst wall closes a plurality of channels in said living tissue adjacent said tissue portion on which said surgical process is performed.

41. The method of claim 40 wherein said channels are selected from the group consisting of: veins, arteries, lymphatic channels, bile ducts, and bronchiole.

42. The method of claim 40 wherein closing said plurality of channels prevents loss of fluid or air from said channels, thereby allowing said method to be completed without a stitching step.

43. The method of claim 42 wherein the portion of live tissue comprises bleeding-prone tissue selected from the group consisting of: spleen, liver, lung, pancreas, kidney, and brain.

44. The method of claim 31 further comprising performing step (d) with at least a portion of said hand-piece tip submerged underwater.

45. The method of claim 31 wherein the surgical procedure comprises a procedure selected from the group consisting of: general surgery, micro-surgery, endoscopic surgery, and laparoscopic surgery.

46. The method of claim 45 wherein the portion of live tissue comprises tissue selected from the group consisting of: liver, spleen, pancreas, lung, stomach, intestines, brain, skin, cartilage, and bone.

47. The method of claim 45 wherein surgical procedure comprises general surgery and the hand-piece has a diameter (D) in the range of about 10 to about 14 mm and a length (L) of about 50 to about 150 mm.

48. The method of claim 45 wherein surgical procedure comprises micro surgery and the hand-piece has a diameter (D) in the range of about 5 to about 8 mm and a length (L) of about 50 to about 120 mm.

49. The method of claim 45 wherein surgical procedure comprises endoscopic or laparoscopic surgery and the hand-piece has a diameter (D) of about 10 mm.

50. The method of claim 45 wherein said apparatus further comprises a control system connected to said inert gas supply and to said power supply, said control system having at least one user interface and a plurality of energy settings, said control system adapted to vary the voltage curve and the inert gas flow to provide a user-selected quantum energy and total energy level in said plasma, said control system comprising a programmable controller, a quantum energy control user interface connected to said programmable controller, and a total energy control user interface connected to said programmable controller, in which the method further comprises:

(f) an operator choosing said predetermined quantum energy level via said quantum energy control user interface;

(g) said operator activating said total energy control user interface to indicate a desired change in total energy level, and (h) said programmable controller controlling said control system to adjust said inert gas flow and an amount of current and voltage supplied by said power supply in response to said desired change indicated by said operator.

51. The method of claim 31 further comprising said high-energy inert gas atoms emitting photons having a visible color indicative of an energy level of said atoms.

52. The method of claim 51 further comprising manually adjusting the energy level of said atoms based upon the visible color to achieve a predetermined color known to be effective for said living tissue.

53. The method of claim 31 wherein said surgical apparatus comprises a plurality of quantum energy settings corresponding to relative energy levels of the emitted high-energy gas atoms and the process comprises resecting a vein or an artery, said method further comprising:

(f) constricting a section of the vessel by using the apparatus at a relatively low energy setting that does not perforate the vessel, and then (g) cutting the constricted section using the apparatus at a relatively higher energy setting.

54. The method of claim 31 wherein step (a) comprises providing an amount of inert gas flow into said plasma cell sufficient to provide a predetermined total energy level for performing said surgical operation.

55. The method of claim 40 wherein closing said plurality of channels prevents transfer of cells or parts of tissue through said channels.

56. The method of claim 55 wherein closing said plurality of channels prevents transfer of cancer cells or parts of tumor tissue through said channels.

57. The apparatus of claim 9 further comprising:

a gas regulator connected to the inert gas source for increasing or decreasing gas flow;

a motor connected to the gas regulator adapted to rotate in a first direction to turn the regulator in the first direction to increase gas flow and adapted to rotate in a second direction to turn the regulator in the second direction to decrease gas flow; and a power source connected to the motor; wherein the first switch for increasing power is adapted to cause the motor to rotate in the first direction when activated and the second switch for decreasing power is adapted to cause the motor to rotate in the second direction when activated.

* * * * *